(12) United States Patent
Carlander et al.

(10) Patent No.: US 12,357,249 B2
(45) Date of Patent: Jul. 15, 2025

(54) ROTATABLE PATIENT POSITIONING APPARATUS

(71) Applicant: Elekta Limited, Crawley (GB)

(72) Inventors: Erik Carlander, Crawley (GB); Maja Nilsson, Crawley (GB); Florian Weber, Crawley (GB)

(73) Assignee: Elekta Limited, Crawley (GB)

( * ) Notice: Subject to any disclaimer, the term of this patent is extended or adjusted under 35 U.S.C. 154(b) by 380 days.

(21) Appl. No.: 17/906,025

(22) PCT Filed: Mar. 11, 2021

(86) PCT No.: PCT/EP2021/056267
§ 371 (c)(1),
(2) Date: Sep. 9, 2022

(87) PCT Pub. No.: WO2021/180895
PCT Pub. Date: Sep. 16, 2021

(65) Prior Publication Data
US 2023/0134952 A1    May 4, 2023

(30) Foreign Application Priority Data
Mar. 11, 2020 (GB) ..................... 2003561

(51) Int. Cl.
*A61B 6/04*        (2006.01)
(52) U.S. Cl.
CPC .................. *A61B 6/0487* (2020.08)
(58) Field of Classification Search
CPC .... A61B 6/0487; A61B 6/0407; A61G 13/04; A61G 13/06
See application file for complete search history.

(56) References Cited

U.S. PATENT DOCUMENTS 2,534,623 A * 12/1950 Pitts .................. A61B 6/04
                                                            5/601
3,069,543 A * 12/1962 Sazavsky ............. A61B 6/0487
                                                            5/601
(Continued)

FOREIGN PATENT DOCUMENTS

CN    202776546 U    3/2013
CN    108100939 A    6/2018
(Continued)

OTHER PUBLICATIONS

"International Application Serial No. PCT/EP2021/056267, International Search Report dated Aug. 11, 2021", (Aug. 11, 2021), 6 pgs.
(Continued)

*Primary Examiner* — Eric J Kurilla
(74) *Attorney, Agent, or Firm* — Schwegman Lundberg & Woessner, P.A.

(57) ABSTRACT

Disclosed herein is a patient positioning apparatus for a medical device. The apparatus comprises a patient support apparatus, a support structure configured to extend between the patient support apparatus and a floor of a treatment room to support the patient support apparatus above the floor of the treatment room. The patient support apparatus is rotationally coupled to the support structure. The patient positioning apparatus comprises a rotation mechanism comprising a drive member and is configured to impart a force, via the drive member, to an underside of the patient support apparatus to thereby rotate the patient support apparatus with respect to the support structure. The rotation mechanism is attached to, and supported by, the support structure.

18 Claims, 20 Drawing Sheets

(56) References Cited

U.S. PATENT DOCUMENTS

| | | | | |
|---|---|---|---|---|
| 3,158,742 | A | * | 11/1964 | Morel ............... A61B 6/0487 378/209 |
| 3,588,500 | A | * | 6/1971 | Koerner ............... A61B 6/10 5/601 |
| 4,131,801 | A | * | 12/1978 | Hogan ............... A61B 6/0487 5/601 |
| 4,449,262 | A | * | 5/1984 | Jahsman ............... A61G 13/06 5/616 |
| 4,613,122 | A | * | 9/1986 | Manabe ............... A61B 6/0487 5/601 |
| 4,773,637 | A | * | 9/1988 | Jarin ............... A61B 6/0487 5/601 |
| 4,984,774 | A | * | 1/1991 | Zupancic ............... A61B 6/0487 5/81.1 R |
| 5,345,632 | A | | 9/1994 | Langenaeken et al. |
| 6,240,582 | B1 | * | 6/2001 | Reinke ............... A61G 13/02 5/601 |
| 2004/0172758 | A1 | | 9/2004 | Alakkat |
| 2007/0289064 | A1 | | 12/2007 | Martin et al. |
| 2008/0082027 | A1 | | 4/2008 | Phillips |
| 2010/0329414 | A1 | | 12/2010 | Zhu et al. |
| 2018/0177469 | A1 | | 6/2018 | Suga |
| 2019/0216550 | A1 | | 7/2019 | Eyre et al. |

FOREIGN PATENT DOCUMENTS

| | | |
|---|---|---|
| CN | 110840692 A | 2/2020 |
| WO | WO-2011015776 A1 | 2/2011 |

OTHER PUBLICATIONS

"International Application Serial No. PCT/EP2021/056267, Written Opinion dated Aug. 11, 2021", (Aug. 11, 2021), 9 pgs.

"United Kingdom Application Serial No. 2003561.4, Examination Report dated Sep. 11, 2020", (Sep. 11, 2020), 8 pgs.

* cited by examiner

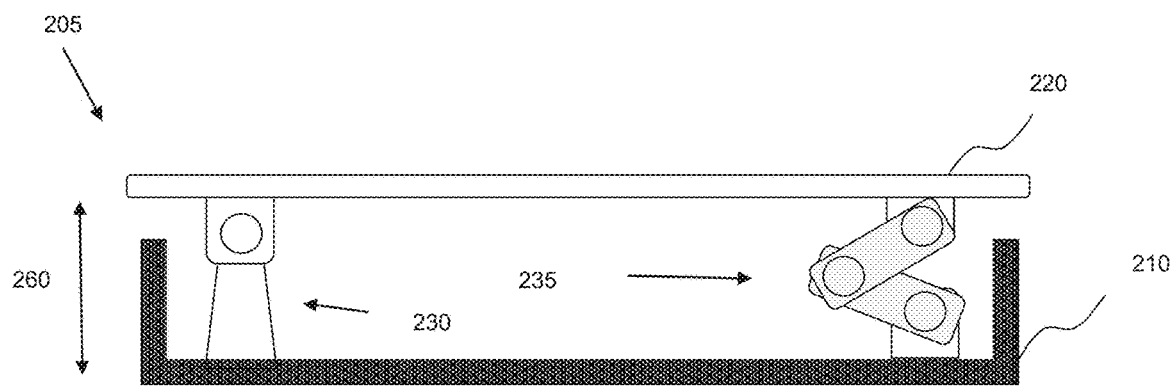
Fig. 2a – Prior Art
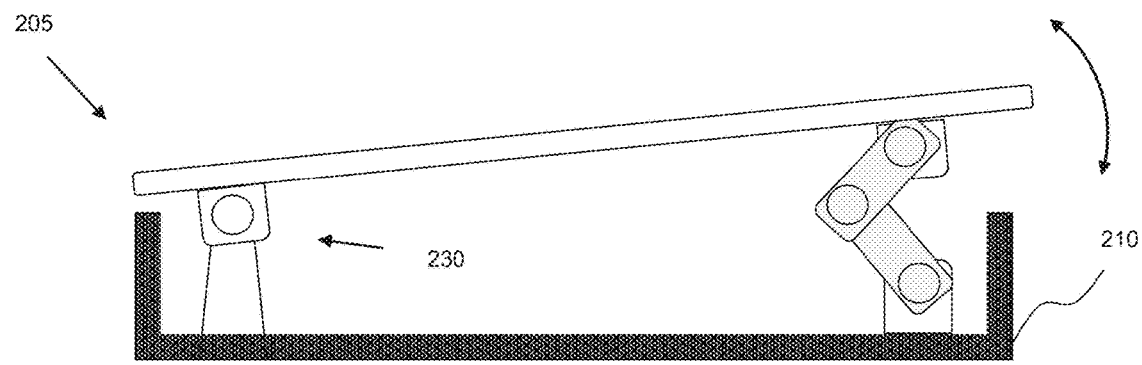
Fig. 2b – Prior Art
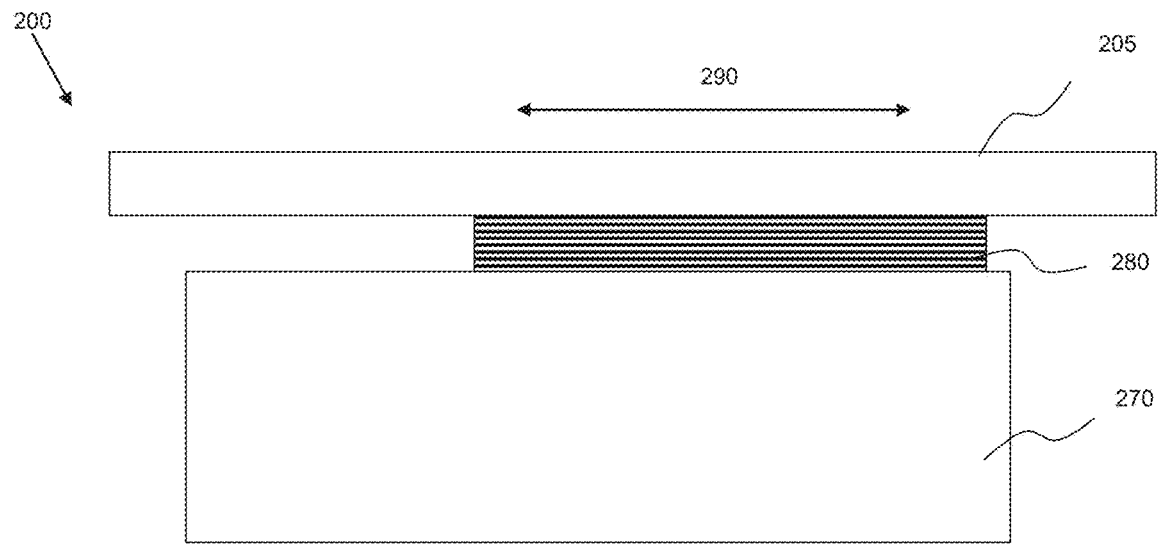
Fig. 2c – Prior Art

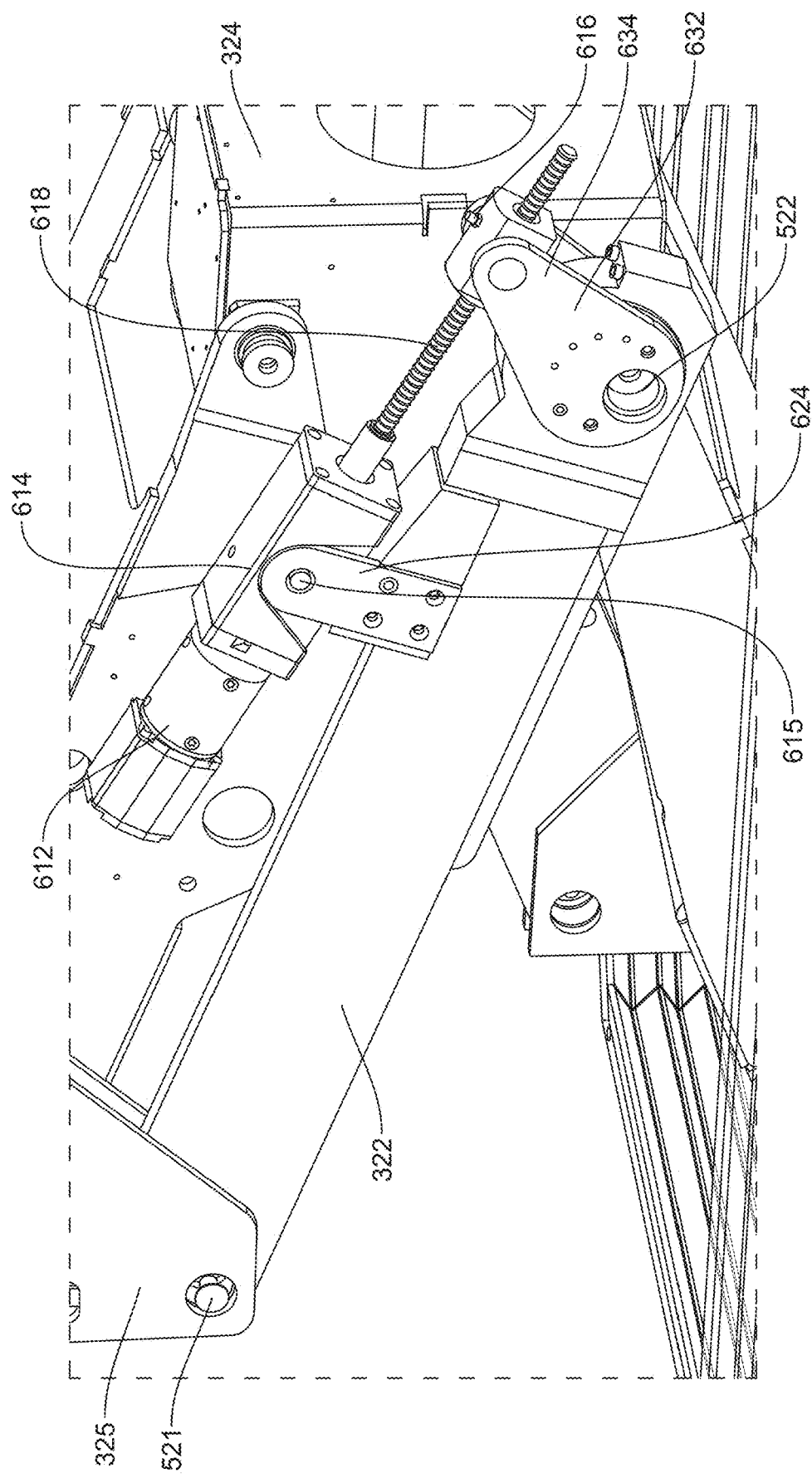

ROTATABLE PATIENT POSITIONING APPARATUS

PRIORITY APPLICATIONS

This application is a U.S. National Stage Filing under 35 U.S.C. § 371 from International Application No. PCT/EP2021/056267, filed on Mar. 11, 2021, and published as WO2021/180895 on Sep. 16, 2021, which claims the benefit of priority to United Kingdom Application No. 2003561.4, filed on Mar. 11, 2020; the benefit of priority of each of which is hereby claimed herein, and which applications and publication are hereby incorporated herein by reference in their entireties.

This disclosure relates to patient positioning apparatuses for a medical device, and in particular to those devices comprising a rotatable patient support apparatus.

BACKGROUND

A patient positioning apparatus may be used to position a patient in a scanning or treatment volume of a medical device. For example, in the field of radiotherapy, a patient positioning apparatus may be used to ensure the patient is correctly positioned with respect to a source of therapeutic radiation in accordance with a treatment plan. The patient positioning apparatus may be configured to move the patient in multiple of degrees of freedom, and this is particularly important in the field of radiotherapy to ensure optimal positioning of the patient and thus to ensure the prescribed dose of radiation is delivered accurately and optimally to a target region.

A number of difficulties arise when designing a patient positioning apparatus which is able to tilt, or rotate. FIG. 2c depicts a prior patient positioning apparatus 200. The positioning apparatus 200 comprises a patient support apparatus 205 which is depicted in further detail in FIGS. 2a and 2b. The support apparatus 205 comprises a base plate 210 and a patient support surface 220. The patient support surface 220 is connected to the base plate 210 via a bearing 230. The bearing 230 (which may be approximately located under the patient's feet, in use) has a rotatory degree of freedom but no translatory degrees of freedom. The front support (which may be approximately located under the patient's head, in use) is an adjustable joint 235 spaced apart from the rear bearing 230. The adjustable joint 235 has a variable height. By adjusting the height of the adjustable joint, the patient support surface 220 can be rotated about an axis of rotation defined by bearing 230. Thus, the patient support surface 220 can be tilted.

However, there are problems associated with this prior arrangement. The separation 260 between the base plate 210 and patient support surface 220 must be sufficiently large to allow the patient support surface 220 to tilt in the desired directions. If a large degree of tilt is required, the separation 260 must be correspondingly large. This results in a large and bulky patient support apparatus 205, which must be supported above the ground by strong legs or other support structure 270.

It is generally important to be able to reduce the so-called 'hop-on height' of the patient positioning surface, i.e. the height which the patient must overcome in order to climb onto the support surface. It is important that this height can be reduced as far as possible to facilitate the patient's climbing onto the surface, particularly as the positioning apparatus must accommodate patients of various ages, heights, and levels of health and physical fitness. The requirement for a large separation 260 adds significant height to the patient support apparatus, and the height of the support apparatus 205 and the correspondingly bulky support structure 270 can both be detrimental to the hop-on height.

Design requirements for a patient positioning apparatus may also call for adjustment of not only a tilt angle of the patient supporting apparatus, but also adjustment of translatory degrees of freedom such as the height and linear position of the patient support apparatus. Positioning a tilting mechanism between a patient support surface 220 and a base plate 210 as depicted in FIGS. 2a and 2b means that, to adjust the linear position of the patient support surface, the position of the base plate 210, bearing 230, and adjustable joint 235 must also be adjusted. In other words, due to the nature of the tiling mechanism depicted in FIGS. 2a and 2b, the support surface 220, the base plate 210, and the rotation mechanism (bearing 230 and adjustable support 235) must all be translated together. Therefore, linear adjustment of the apparatus 205 in a translatory degree of freedom, as depicted by arrow 290 in FIG. 2c, is made more difficult by the weight and size of the support apparatus 205. In turn, correspondingly large linear actuation mechanisms 280 are required, which must be configured to bear a heavy load. It has been difficult to effectively manage this load in prior apparatuses, resulting in large bulky devices.

The present invention(s) seek to address these and other disadvantages encountered in the prior art.

SUMMARY

Aspects of the invention are defined in the independent claims. Optional features are defined in the dependent claims.

According to an aspect, a patient positioning apparatus for a medical device is provided. The apparatus comprises a patient support apparatus and a support structure configured to extend between the patient support apparatus and a floor of a treatment room to support the patient support apparatus above the floor of the treatment room. The patient support apparatus is rotationally coupled to the support structure. The apparatus further comprises a rotation mechanism comprising a drive member and configured to impart a force, via the drive member, to an underside of the patient support apparatus to thereby rotate the patient support apparatus with respect to the support structure. The rotation mechanism is attached to, and supported by, the support structure.

According to another aspect, a patient positioning apparatus for a medical device is provided. The patient positioning device comprises a tiltable patient support apparatus and a sensor arrangement. The sensor arrangement comprises a processor, and a first and a second sensor communicatively coupled to the processor. The sensors are spaced from one another, the first sensor being configured to provide signals indicative of a first distance between a first region of the underside of the patient support apparatus and a first fixed location underneath the patient support apparatus, and the second sensor being configured to provide signals indicative of a second distance between a second region of the underside of the patient support apparatus and a second fixed location underneath the patient support apparatus. The processor is configured to determine, based on signals from the sensors, a degree of tilt of the patient support apparatus.

According to another aspect, a patient support apparatus for tilting a patient support surface about a tilt axis is provided. The apparatus comprises a patient support base and a rotation mechanism comprising a first swing element and a second swing element, wherein each swing element is configured to rotate about its axis of rotation and each swing element extends radially outward from its axis of rotation. The rotation mechanism is configured to rotate the first and second swing element. The apparatus further comprises a patient support surface comprising a first and a second coupling member, the first coupling member being rotationally coupled to an end of the first swing element distal to the axis of rotation of the first swing element and the second coupling member being rotationally coupled to an end of the second swing element distal to the axis of rotation of the second swing element. By rotating each swing element in a first direction, the rotation mechanism causes the patient support surface to tilt in a second direction with respect to the base structure. By rotating each swing element in the second direction, the rotation mechanism causes the patient support surface to tilt in the first direction with respect to the base structure.

FIGURES

Specific embodiments are now described, by way of example only, with reference to the drawings, in which:

FIG. 1 depicts a radiotherapy device or apparatus comprising a patient positioning apparatus according to the present disclosure;

FIGS. 2a-c depict a prior arrangement;

FIGS. 3a-c depict a patient positioning apparatus according to a first implementation of the present disclosure;

FIGS. 4a,b depict a patient positioning apparatus at different tilt angles, according to the first implementation of the present disclosure;

FIGS. 5a-b depict opposing side views of the patient positioning apparatus according to the first implementation of the present disclosure.

FIG. 6 depicts a rotation mechanism according to the first implementation;

FIGS. 7a-b depict a cross section through a motion converter and a drive member of the rotation mechanism depicted in FIG. 6;

DETAILED DESCRIPTION

The present application relates to a patient positioning apparatus for a medical device, preferably a radiotherapy device. The patient positioning apparatus comprises a patient support apparatus configured to rotate about a support structure. In use, a patient lies on an upper surface of the patient support apparatus. The support structure extends between the patient support apparatus and the floor of the treatment room in order to provide support to the patient support apparatus, and in particular in order to support the patient support apparatus above the floor of the treatment room.

Rather than providing a rotation mechanism as part of the patient support apparatus, as in prior arrangements, the rotation mechanism of the present disclosure is instead attached to, and supported by, this support structure. By moving the rotation mechanism out from the same plane as the patient support apparatus and fixing the rotation mechanism to the support structure, e.g. to support legs which are configured to bear the weight of the patient support apparatus, the hop-on height of the patient positioning apparatus is reduced, and the degree to which the patient support apparatus can be tilted is increased as there are fewer mechanical impediments to the rotation. Also, by providing a rotation mechanism attached to, and supported by, the support structure in this way, the mechanism is easier to access and maintain.

In some implementations of this apparatus, the patient support apparatus comprises a support surface which is moveable in a linear direction with respect to a patient support base. By removing the rotation mechanism from between these two layers and instead positioning it underneath the patient support base in the manner described herein, this linear movement is greatly facilitated and a simpler mechanism may be provided. In particular, it is no longer required to translate the entire rotation mechanism, which can instead remain stationary as the patient support surface translates with respect to the patient support base.

Also, in prior designs, during rotation of the patient support apparatus the entire weight of the patient support apparatus must be born by the rotation mechanism. In the present design, this weight may instead be borne by the support structure. Accordingly, mechanical wear and tear is reduced, which in turn reduces the chances of breakdown and increases the longevity of the apparatus.

A Radiotherapy Device

The patient positioning apparatuses described herein may be used in conjunction with a medical device, for example an imaging device. In a preferred implementation, the medical device is a radiotherapy device.

Figure 1:
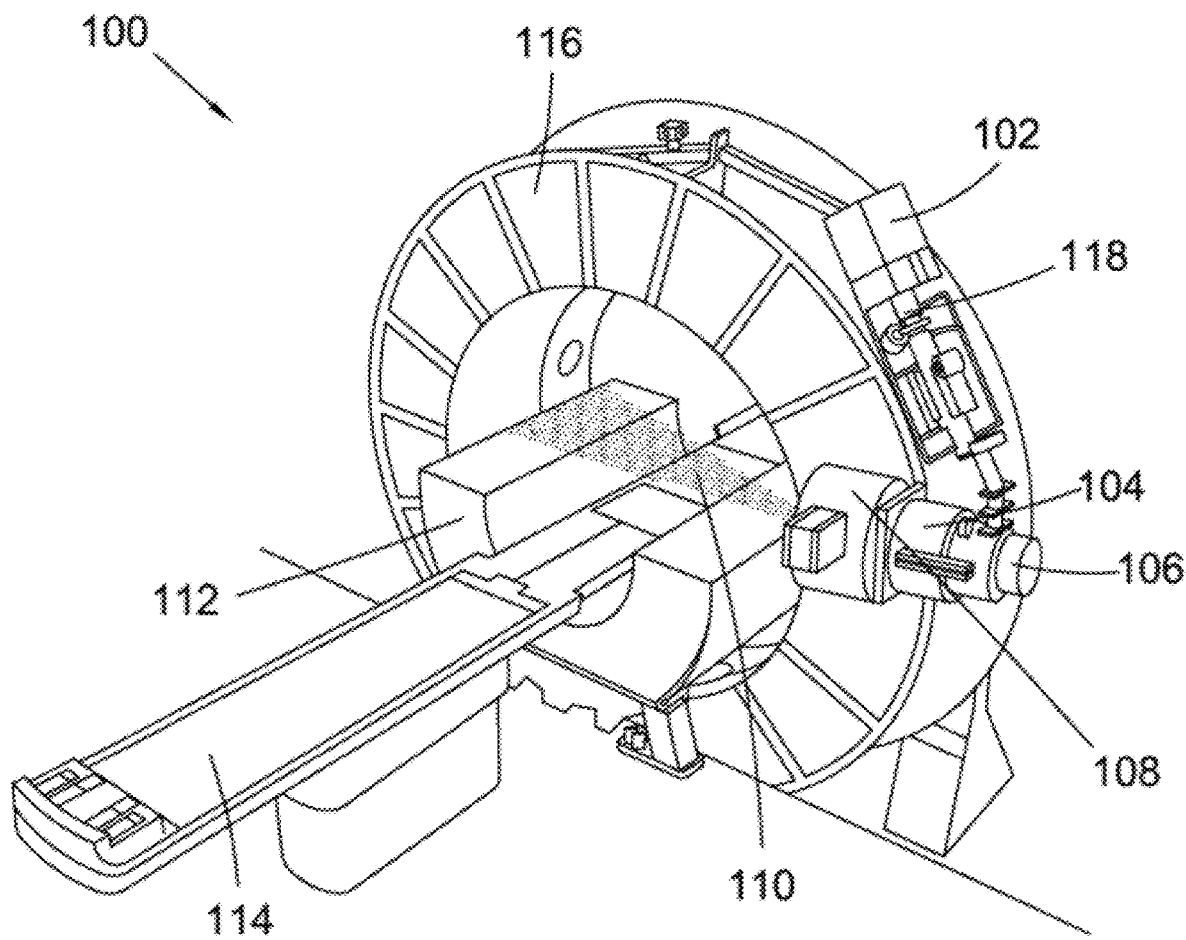

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The patient positioning apparatus of the present disclosure may be used to position a patient in the treatment and/or imaging volume of the device depicted in FIG. 1.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient positioning apparatus comprising a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104.

Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the subject support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

Figure 3A:
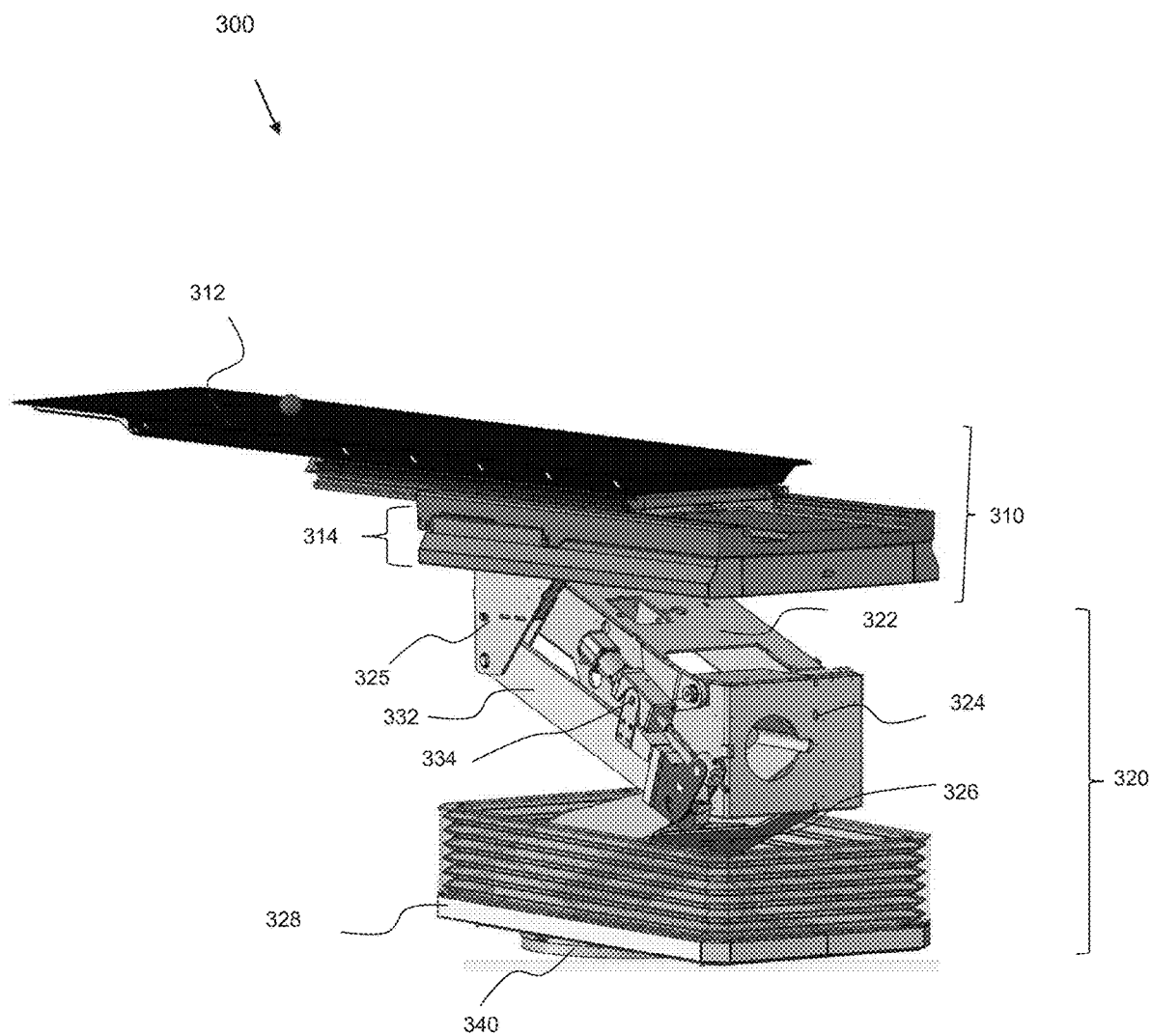
Figure 3B:
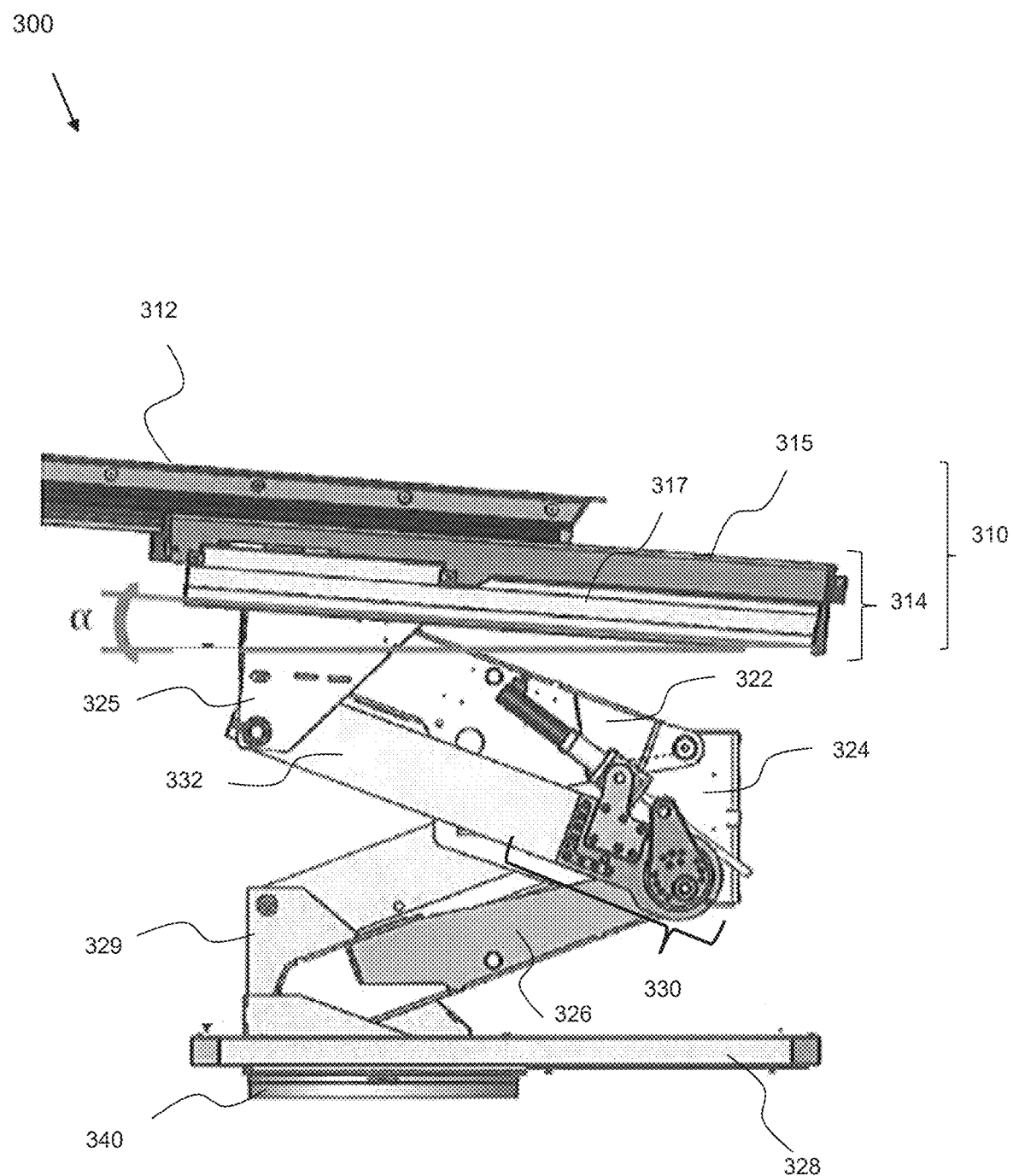
Figure 3C:
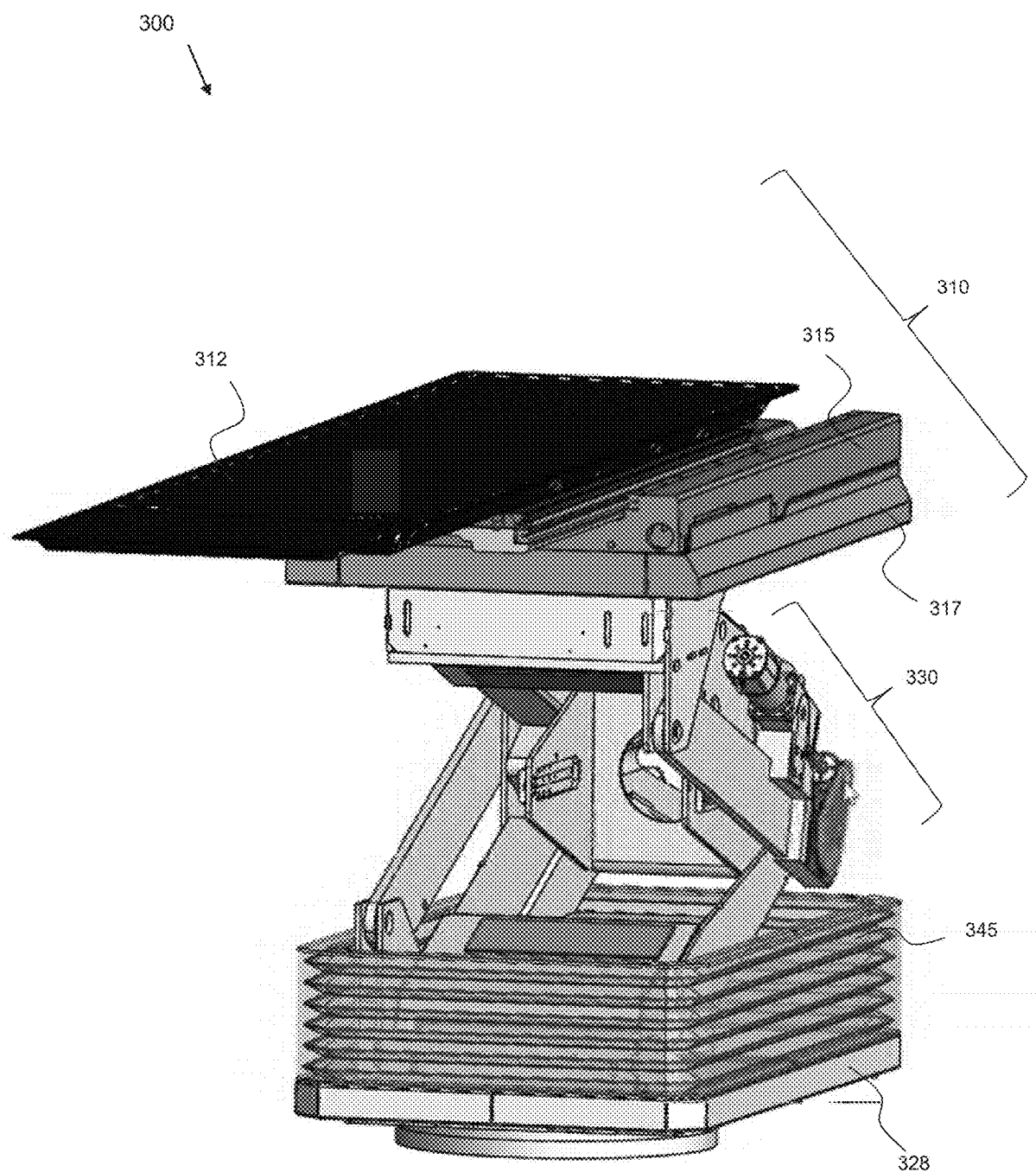

FIGS. 3a, 3b, and 3c depict a patient positioning apparatus 300 according to the present disclosure. FIG. 3a depicts an angled rear view of the patient positioning apparatus 300. FIG. 3b depicts a side-on view of the positioning apparatus 300. FIG. 3c depicts an angled front view of the positioning apparatus 300. The patient positioning apparatus 300 comprises a patient support apparatus 310 and a support structure 320. The support structure 320 is configured to support the patient support apparatus 310 above a floor, such as the floor of a treatment room. The support structure 320 may be configured to provide this support, in part, by means of a base 328 which contacts the floor, and/or which is embeddable within the floor. In the implementation depicted in FIGS. 3a-c, the support structure comprises a first, or upper, supporting leg 322, a support element 324, and a second, or lower, supporting leg 326.

The patient positioning apparatus 300 also comprises a rotation mechanism. The rotation mechanism is configured to tilt, i.e. rotate, the patient support apparatus 310. The rotation is made with respect to a horizontal plane, or equivalently with respect to the floor of the treatment room, in order to adjust a tilt angle, for example a pitch angle marked a in FIG. 3b. In the implementation depicted in FIGS. 3 a-c, the rotation mechanism comprises a drive member 332 and an actuation mechanism 330. The rotation mechanism is configured to impart a force, via the drive member 332, to an underside of the patient support apparatus 310 to thereby rotate the patient support apparatus 310 with respect to the support structure 320.

The patient support apparatus 310 is configured to support a patient. The patient support apparatus 310 comprises a patient support surface 312 and a patient support base 314. In use of the apparatus, a patient may lie on the patient support surface 312. In other words, in use, the patient contacts an upper surface of the patient support apparatus 310. The patient support surface 312 can be moved linearly with respect to the patient support base 314 along an axis parallel with the longitudinal axis of the patient support apparatus 310. The directions of this linear movement are indicated by the double-headed arrow 510 in FIG. 5. The patient positioning apparatus 300 may be configured to rotate the patient support surface 312 with respect to one or both of a pitch and a roll rotation axis (see FIG. 11 and accompanying description below). In such an implementation, the axis of linear movement of the patient support surface 312 with respect to the patient support base 314 is parallel with and/or aligns with the roll rotation axis.

This movement may be controlled via a linear actuator or suitable actuation mechanism 330, and the patient support surface 312 is coupled with other components of the patient support apparatus 310, such as the patient support base 314, in order to facilitate this movement. This linear movement may be described as a translation. In other words, the patient support surface 312 is configured to translate linearly with respect to the patient support base 314.

For example, as can be seen best in FIG. 3c, the patient support base 314 may comprise upper base structure 315, such as an upper lateral sledge, and lower base structure 317, such as a lower lateral sledge. Together, the upper and lower base structures 315 and 317 form the patient support base 314. The patient support surface 312 comprises a longitudinal extension, or ridge. The longitudinal extension extends downward from a lower surface of the patient support surface. The patient support base 314, and in particular the upper base structure 315, comprises a corresponding longitudinal groove. The longitudinal groove is formed on an upper surface of the upper base structure 315. The longitudinal ridge is inserted in the groove in order to couple the patient support surface 312 to the upper base structure 315, but so as to allow movement of the patient support surface 312 with respect to the patient support base 324 along an axis defined by the longitudinal groove. Movement of the patient support surface 312 with respect to the patient support base is controlled via a linear actuator, such that the patient support surface 312 is configured to move in a longitudinal, linear manner with respect to the patient support base 314 and the other components of the patient positioning apparatus 300. It will be appreciated that the ridge and groove arrangement may be swapped in some implementations such that the support surface comprises the groove and the support base comprises the corresponding ridge.

In addition or as an alternative to a longitudinal movement, the patient positioning surface may also be configured to move laterally. This movement is perpendicular to the longitudinal movement, and can be controlled via movement of the upper lateral sledge 315 with respect to the lower lateral sledge 317. This movement can be effected by actuators in a known way. In summary then, the patient support surface 312 may be configured to move in any, all, or a combination of three translator degrees of freedom: height, a longitudinal movement (parallel to roll axis 1120 shown in FIG. 11) and a lateral movement (parallel to pitch axis 1110 shown in FIG. 11).

The rotation mechanism is configured to rotate the patient support apparatus 310, i.e. both the patient support surface 312 and the patient support base 314. Because the rotation mechanism is coupled to and supported by the support structure 320 and positioned underneath the patient support apparatus 310, rather than forming part of the patient support apparatus 310 as in previous designs, the weight and size of the patient support apparatus 310 can be significantly reduced. Because the rotation mechanism does not form part of the patient support apparatus 310, it is not necessary to translate the entire patient support apparatus 310 (including the rotation mechanism) as part of the linear translation of the patient support surface 312, as in previous designs such as that depicted in FIGS. 2a-c. The rotational coupling which defines the rotation axis of the patient support apparatus 310 is positioned underneath the main body of the patient support apparatus 310, and in particular the base of the patient support apparatus 310 is coupled to a support structure 320 configure. Thereby, the linear translation of the patient can be achieved by translating a relatively light patient support surface 312 with respect to the patient support base 314. Accordingly, the load which the translation motor must bear is reduced, while the ability to control the tilt angle of the patient support apparatus 310 is maintained.

The support structure 320 is configured to bear the weight of the patient support apparatus 310, as well as a patient positioned on the patient support surface 312. Multiple implementations of the support structure 320 are envisaged. In the implementation depicted in FIGS. 3 and 4, the support structure 320 comprises an upper element coupled to an underside of the patient support apparatus 310, and a lower element coupled to the base. The upper element may be a first supporting leg 322 and the lower element may be a second supporting leg 326 coupled to the base. The first supporting leg 322 and second supporting leg 326 are coupled to one another via a support element 324. The support element 324 may be referred to as a support block or anchor element herein.

The patient support apparatus 310 is rotationally coupled to the support structure 320 to allow rotation about a rotation axis. In a simple implementation, the support structure 320 may be coupled to the patient support apparatus 310 via the interaction between a shaft and one or more bearings which receive the shaft. For example, the one or more bearings may be mounted to an underside of the patient support apparatus 310, and configured to receive a shaft which forms part of the support surface. For example, an upper region of the first supporting leg 322 may culminate in a double-ended shaft, with each end of the shaft being received in a bearing mounted to a base of the patient support apparatus 310. In this implementation, the orientation of the shaft and bearings defines an axis of rotation about which the patient support apparatus 310 may rotate with respect to the support structure 320. Other implementations include a ball-joint, or any other mechanical connection that allows rotation of the patient support apparatus 310 with respect to the support surface via a rotation axis.

A second, or lower, supporting leg is coupled to the base. The second supporting leg 326 may be fixedly attached to the base. Alternatively, the coupling may be achieved via a lower coupling element and the second supporting leg 326 may be configured to rotate with respect to the lower coupling element as part of a height adjustment mechanism. The lower coupling element extends upward out of the plane of the base, allowing the second supporting leg 326 to be coupled to the lower coupling element to define a rotation axis parallel with the rotation axis about which the patient support apparatus 310 rotates with respect to the first supporting leg 322.

The support structure 320 may also comprise a height adjustment mechanism (not shown in the figures). The height adjustment mechanism is configured to adjust the height, i.e. vertical distance, of the patient support apparatus 310 above the floor or base. The height adjustment mechanism comprises one or more motor mechanisms. An upper motor mechanism may be positioned within, form part of, or be coupled to, the support element 324. A lower motor mechanism may be positioned within, form part of, or be coupled to, the lower coupling element.

The height adjustment mechanism may be formed by one or multiple different mechanisms. In the implementation depicted in FIGS. 3a-c and 4a-b, the height adjustment mechanism is configured to adjust the vertical distance between the support element 324 and the patient support apparatus 310 by actuating the first supporting leg 322. Thereby, the height of the patient support apparatus 310 above the floor is increased. The height adjustment mechanism comprises a rotational mechanism or motor configured to produce a rotary motion of the first supporting leg 322 with respect to the support element 324. This may be a rotary hydraulic motor. This rotary motor is housed within the support element 324. It will be appreciated that by rotating the first supporting leg 322 clockwise from the perspective shown in FIG. 4, the height of the patient support apparatus 310 above the floor/base is increased.

Optionally, an additional rotary motor may be provided. This rotary motor may be referred to as a 'lower' rotary motor in contrast to the 'upper' rotary motor described above. The lower rotary motor is also housed within the support element 324 and is configured to drive rotation with respect to the support element 324 and the lower leg 326. The height adjustment mechanism may thereby also be configured to adjust the vertical distance between the support element 324 and the base 328 and/or floor of the treatment room, by actuating the second supporting leg 326 using this lower rotary motor. Thereby, the height of the patient support apparatus 310 is adjusted. By schronously driving rotation using both the upper and the lower rotary motor, the vertical height of the patient support surface 312 may be adjusted.

For example, the height adjustment mechanism may comprise a lower rotational mechanism or motor, e.g. a rotary hydraulic motor, configured to produce a rotary motion of the second supporting leg 326 with respect to the support structure 324. It will be appreciated that by rotating the second supporting leg 326 anti-clockwise, from the perspective shown in FIG. 3b, the height of the patient support apparatus 310 above the base is increased.

The height adjustment mechanism is configured to control a height of the patient support apparatus 310 above the floor of the treatment room. As described above, the patient support apparatus 310, and in particular the base of the patient support apparatus 310, is rotationally coupled to the support structure 320 to allow rotation about a rotation axis. By adjusting the height of the patient support apparatus 310 above the floor of the treatment room using the height adjustment mechanism, the height of this rotation axis can also be adjusted.

While a support structure 320 and height adjustment mechanism has been described which comprises a mechanism capable of rotating one or a plurality of supporting legs about rotation axes in order to adjust the height of the patient support apparatus 310, the height adjustment mechanism may take multiple forms. For example, the height adjustment mechanism may comprise an arrangement of hydraulic pistons positioned and configured to adjust the height of the patient support apparatus 310. An alternative implementation may involve a scissor lift mechanism. The skilled person will be aware of other possible ways in which the height of a patient support apparatus 310 may be adjusted. Regardless of the specific implementation of the support structure 320 and/or height adjustment mechanism, the rotation mechanism is coupled to the support structure 320 and is configured to impart a force to an underside of the patient support apparatus 310 in order to rotate the patient support apparatus 310 with respect to the support structure 320.

In some implementations, the positioning apparatus 300 also comprises a skirt 345 (not shown in FIG. 3b) configured to cover the support structure 320 and rotation mechanism. The skirt 345 is connectable between the base 328 and the patient support apparatus 310. The skirt 345 has a flexibility, and in particular may have a concertina configured, i.e. be configured to extend, compress, or collapse in folds like those of a concertina. Thus, patients and clinicians are protected from injury by virtue of the moving mechanisms described herein. It is simpler to provide this protection using a simple skirt 345 by virtue of the present design, and in particular by virtue of the rotation mechanism being attached to and supported by the support structure. In FIGS. 3a and 3c, the skirt is folded or compressed down away from the patient support apparatus 310 so that the support structure 320 and rotation mechanism can be seen.

Rotation Mechanism

The patient positioning apparatus 300 also comprises a rotation mechanism. The rotation mechanism is configured to rotate, i.e. tilt, the patient support apparatus 310. The rotation mechanism controls the angle of tilt. The rotation mechanism comprises a drive member 332 and an actuation mechanism 330. The rotation mechanism may also comprise a coupling element 325 which couples the drive member 332 to the patient support apparatus 310.

Figure 4A:
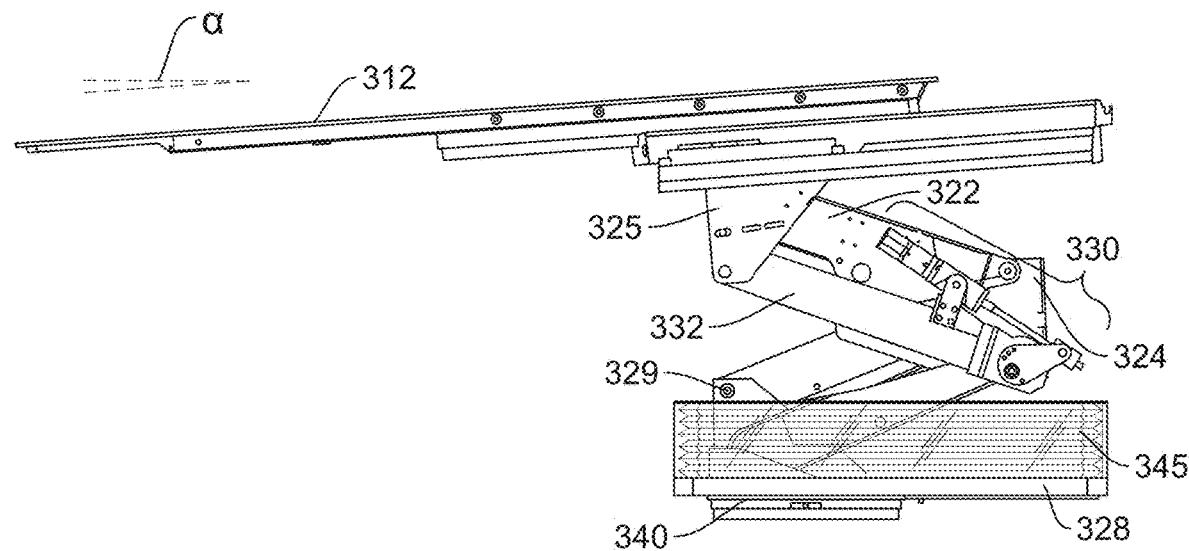
Figure 4B:
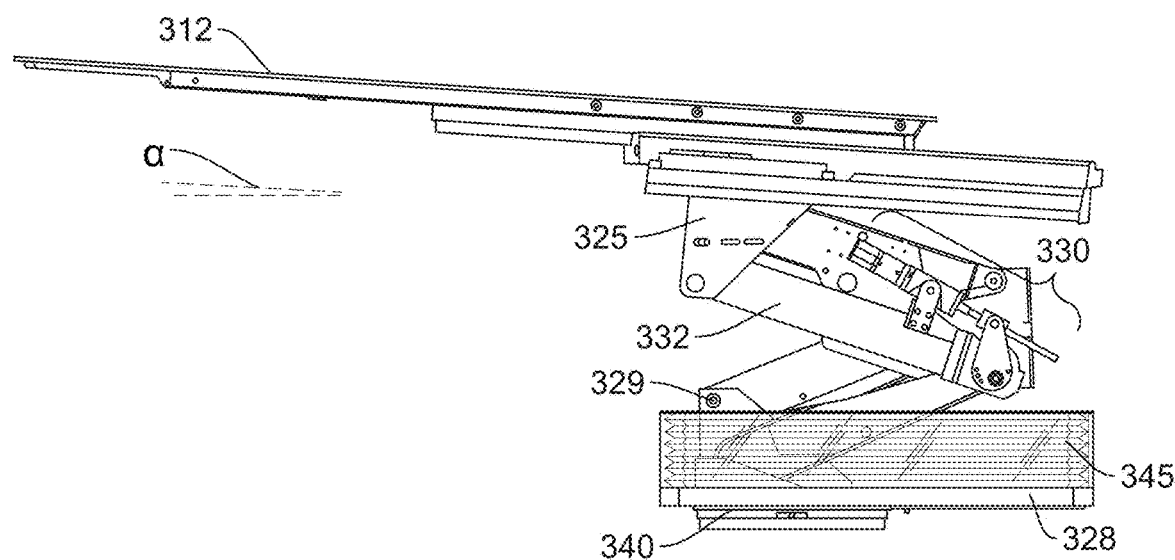

Two example extremes of tilt are depicted in FIGS. 4a and 4b. The tilt angle is depicted using a. The tilt angle is measured with respect to a horizontal plane, or equivalently with respect to the floor of the treatment room. The tilt angle α is the angle which the patient support surface 312 makes with respect to the horizontal plane. In FIGS. 4a and 4b, the 'type' of tilt is a rotation about a pitch axis, and may be referred to as a pitch rotation. In FIG. 4a, the front of the patient support surface 312 has been tilted down. The patient support apparatus of FIG. 4a is at maximum tilt angle α in this negative direction. In FIG. 4b, the front of the patient support surface 312 has been tilted upwards. The patient support apparatus of FIG. 4a is at maximum tilt angle α in this positive direction.

The rotation mechanism may take multiple different forms, though in each it is configured to impart a force to the patient support apparatus 310. By rotationally coupling the patient support apparatus 310 to the support structure 320 to define a rotation axis, and by providing a rotation mechanism which imparts a force to the patient support apparatus 310, a torque may be created about the rotation axis. By controlling the force imparted to the patient support apparatus 310, the torque created about the rotation axis may be controlled, and thus the degree of tilt of the patient support apparatus 310 about the rotation axis may be controlled. Herein, the rotation axis formed between the patient support apparatus 310 and the support structure 320 may be described as the principal rotation axis.

The movement of the drive member 332 occurs along the longitudinal axis of the drive member 332, and the drive member 332 can impart a 'push' force or a 'pull' force. The drive member 332 is coupled to an underside of the patient support apparatus 310, and the direction of tilt can thus be controlled by the direction of movement of the drive member 332. With reference to the viewpoint depicted in FIGS. 3b and 4a, 4b, by pushing/moving the drive member 332 toward the underside of the patient support apparatus 310, a clockwise tilt about the principal axis can be achieved. By pulling/moving the drive member 332 away from the underside of the patient support apparatus 310, an anti-clockwise rotation about the principal axis may be achieved.

The drive member 332 is rotationally coupled to the coupling element 325 at a first (drive member 332) coupling point. The drive member 332 is rotationally coupled to the support element 324 at a second (drive member 332) coupling point. The actuation mechanism 330 is configured to move the drive member 332. More specifically, the actuation mechanism 330 is configured to control, e.g. adjust, a distance between the first and the second drive member coupling points. The first coupling point may be described as an upper coupling point, and the second coupling point may be described as a lower coupling point. The second coupling point is at a fixed position with respect to the support element 324, and therefore by adjusting this distance the location of the first coupling point is controlled by the actuation mechanism 330.

As the actuation mechanism 330 adjusts the distance between the first and second coupling point, the distance between the first coupling point and the support element 324 is also adjusted. By increasing the distance between the first and second coupling points, the first coupling point, and thus the coupling element, is pushed away from the support element 324 of the support structure 320. Conversely, by reducing the distance between the first and second coupling points, the first coupling point, and thus the coupling element 325, are pulled toward the support element 324 of the support structure 320.

The coupling element 325 extends along an underside of the patient support apparatus 310, in particular along an underside of the patient support base 314, in a direction of the longitudinal axis of the patient support apparatus 310. The coupling element 325 also extends away from an underside of the patient support apparatus 310 in a direction substantially perpendicular to the plane of the patient support apparatus 310. Extension in this direction provides sufficient surface area for the coupling element 325 to be coupled to the first supporting leg 332 at the first (drive member 332) coupling point. Optionally, the coupling member 325 may also be rotationally coupled to the support structure 330 to allow rotation of the coupling member 325 about the principal rotation axis.

Summary of Movement and the Various Axes of Rotation

Figure 5A:
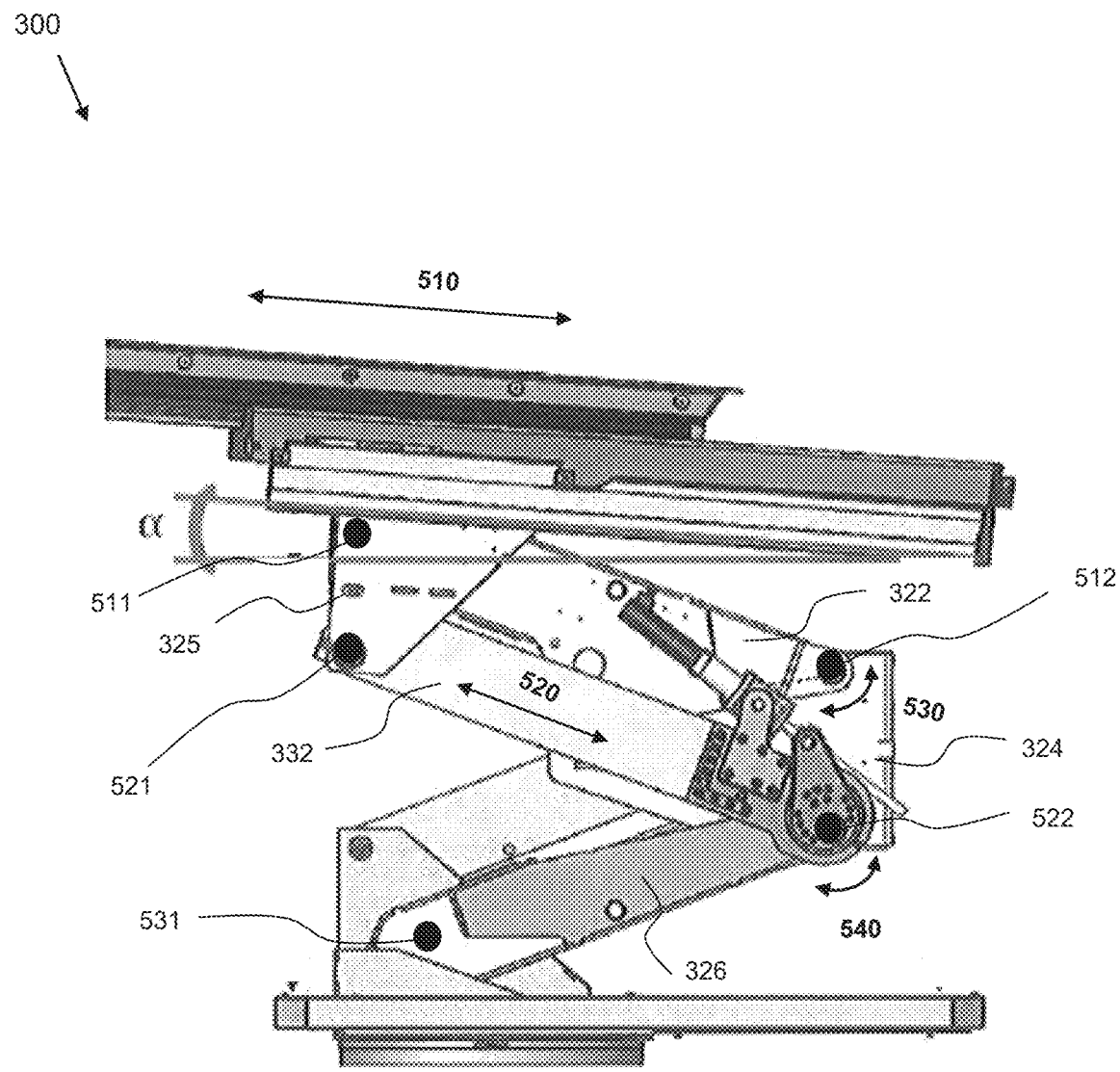

Above, the actions and configurations of a height adjustment mechanism and a rotation mechanism have been described. The resulting directions of movement and the driven axes of rotation may be summarised by reference to FIGS. 5a and 5b. As shown in FIG. 5a, which depicts the same implementation shown in FIGS. 3a-c and 4a-b, the drive member extends between the (upper) coupling element 325 and the support element 324, and is rotationally coupled to these elements. The drive member 332 is rotationally coupled to the coupling element 325 at a first (drive member) coupling point 521, and rotationally coupled to the support element 324 at a second (drive member) coupling point 522. The rotation mechanism is configured to adjust the distance between these two coupling points. Adjusting the distance between the first drive member coupling point 521 and the second drive member coupling point 522 causes the drive member 332 to move. Adjusting the distance between the first drive member 332 coupling point 521 and the second drive member coupling point 522 as measured along the longitudinal axis of the drive member 332 causes the drive member 532 to move along its longitudinal axis.

In an implementation, the drive member 332 comprises an aperture which extends in a direction along the longitudinal axis of the drive member 332, and the drive member 332 is rotationally coupled to the support element 324 by means of this aperture. The support element 324 comprises a fixed spindle, or axle, that defines the location of the second drive member coupling point 522. The fixed spindle, or axle, is fixedly attached to the support element 324 and its location is fixed with respect to the support element 324. The fixed spindle/axle slots into the aperture to allow rotation of the drive member 332 with respect to the supporting element 324. Thus, the second coupling point 522 is fixed with respect to the support element 324. However, by moving the drive member 332 in a direction along the longitudinal axis of the drive member 332, the position of the fixed spindle or axle within the aperture moves. The actuation mechanism 330 of the rotation mechanism controls this movement. Linear movement of the drive member 332 is depicted by arrow 520 in FIG. 5a. Specific implementations of the rotation mechanism and second (drive member) coupling point 522 are described herein with respect to FIGS. 6, 7a-b, 8a-b, and 9a-b.

The upper supporting leg 322 extends between the underside of the patient support apparatus 310 and the support element 324. As with the drive member 332, the supporting leg 322 is rotationally coupled at each end. The upper supporting leg 322 is rotationally coupled to the base of the patient support apparatus 310 at a first (supporting leg) coupling point 511. The first (supporting leg) coupling point 511 defines a principal, or primary, rotation axis. The first (supporting leg) coupling point 511 may be described as the principal, or primary, coupling point. Rotation about this principal axis adjusts the tilt angle α of the patient support apparatus. With respect to FIG. 11, the first (supporting leg) coupling point 511 may define the pitch rotation axis.

The upper supporting leg 322 is rotationally coupled to the support element 324 at a second (supporting leg) coupling point 512. The second (supporting leg) coupling point 512 is located above the second (drive member) coupling point 522 on the support element 324. The support element 324 acts as an anchor and may be held stationary (e.g. by the lower supporting leg 326) while the drive member 332 and the upper supporting leg 322 rotate.

By defining the first and second supporting leg coupling points 511, 512 and the first and second drive member coupling points 521, 522, it is possible to view these points as being the vertices of a parallelogram. The sides, or edges, of the parallelogram may be defined by first opposing sides (drive member 332 and supporting leg 322) and second opposing sides (coupling element 325 and support element 324). The rotation mechanism is configured to control the distance between the first and second drive member coupling points 521, 522 and thus is configured to adjust the length of one of the edges of the parallelogram. By adjusting this length, the angles made between the coupling member 325 and both the drive member 332 and the upper supporting leg 322 are adjusted. This adjusts the orientation of the coupling element 325 with respect to the supporting element 324. Because the coupling element 325 is fixedly attached to the base 314 of the patient support apparatus 310, this in turn causes the patient support apparatus 310 to rotate about the principal rotation axis.

The lower supporting leg 326 is rotationally coupled to the lower coupling element 329 at lower supporting leg coupling point 531. The lower supporting leg 326 is also rotationally coupled to the supporting element 324 at coupling point 522. Thus, the spindle or axle which defines coupling point 522 is configured to couple together the lower supporting leg 522, the supporting element 324, and the drive member 332.

Figure 5B:
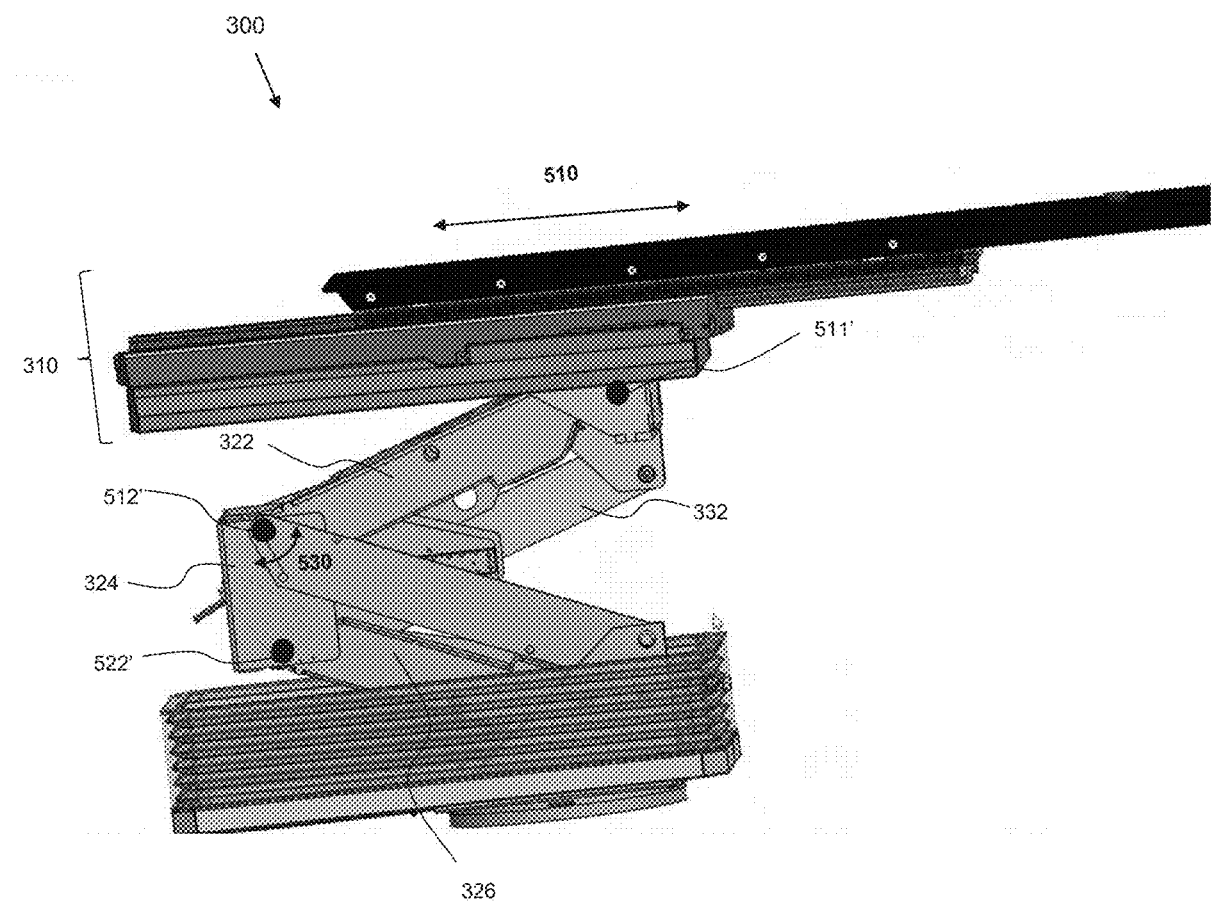

FIG. 5b is a side view depicting the opposite side of the patient positioning apparatus 300 in comparison to the side shown in FIG. 5a. This side is much like the side depicted in FIG. 5a, though the rotation mechanism is not positioned on this side. An axle, spindle or other rotational coupling member defines the position 511' at which the upper supporting leg 322 is rotationally coupled to the patient support apparatus 310. Like reference numerals depict like features.

The coupling points may be described as rotational coupling points, and may be defined by any of a number of rotational coupling mechanisms and structures, for example extending rods, axles or spindles which are received in a suitably sized, positioned and configured bearing or aperture. The specific manner in which each individual coupling point is achieved need not be described in detail as the skilled person will be familiar with ways in which to couple two elements together in order to achieve rotation.

While reference is made to coupling 'points', a limited and narrow meaning of the word 'point' is not intended. It should instead be understood that these coupling points define rotational axes. For example, the upper supporting leg 322 may be rotationally coupled to the support element 324 at two different points, e.g. the coupling point 512 depicted in FIG. 5a and the coupling point 512' depicted in FIG. 5b may be different points in space. However, these points 512, 512' together define a rotational axis about which the upper supporting leg 322 may rotate with respect to the supporting element 324.

As described above, the actuation mechanism 330 of the rotation mechanism is configured to impart a force to the patient support apparatus 310 via the drive member 332. This is accomplished by moving the drive member 332, which in turn is attached, i.e. coupled, to the underside of the patient support apparatus 310. The actuation mechanism 330 moves the drive member 332 in a direction defined by a longitudinal axis of the drive member 332. The drive force can be described as a push, or a pull, depending on its direction. The rotation mechanism is configured to push the drive member 332 toward the coupling element 325, as well as to pull the drive member 332 away from the coupling element 325. Movement of the drive member 332, as controlled by the actuation mechanism 330, is depicted using arrow 520 in FIG. 5a.

As described above, the height adjustment mechanism may control the height of the patient support apparatus 310 by controlling rotation of the upper supporting leg 322 with respect to the support element 324. This rotation occurs about the second supporting leg coupling point 512 and is driven by a rotary motor. This rotation is depicted by arrow 530 in FIG. 5. Alternatively, or additionally, the height adjustment mechanism may comprise another rotary motor configured to rotate the lower supporting leg 326 with respect to the support element 324. This rotation occurs around the second drive member coupling point 522 and is depicted by arrow 540 in FIG. 5. The height can thus be controlled by rotation of one or more rotary motors configured to rotate the supporting legs 322, 326 both upward and downward. By synchronously driving rotation about axes depicted by arrows 530 and 540, the vertical height of the patient support surface can be adjusted without also adjusting the longitudinal or lateral position of the patient support surface 312.

From the above description, it should be appreciated that the drive member 332 is configured to move in three degrees of freedom, a translatory degree of freedom along a longitudinal axis of the drive member 332 as described by arrow 520, and two rotational degrees of freedom. The drive member 322 may rotate about an axis defined by the first drive member coupling point 521 to define a first degree of freedom, and rotate about an axis defined by the second drive member coupling point 522 to define a second degree of freedom. The drive member 332 is driven in the translatory degree of freedom by the rotation mechanism 330. The drive member 332 is not driven about the rotational degrees of freedom, but instead freely rotates about these rotational axes as the height adjustment mechanism adjusts the height of the patient support apparatus 310. In more detail: as the height adjustment mechanism drives the upper supporting leg 322 upwards by rotating 530 the upper supporting leg 322 about its second coupling point 522, the height of the patient support apparatus increases. As an upper portion of the drive member 332 is coupled to an underside of the patient support apparatus via coupling element 325, the drive member is pulled upwards by movement of the patient support apparatus 310. To account for this movement, the drive member 332 rotates about its upper (first) coupling point 511 and its lower (second) coupling point 522. Thus, the drive member 332 is always positioned to effect tilting of the patient support apparatus 310 regardless of the height of the patient support apparatus 310.

Control of the height of the patient support apparatus 310 by the height adjustment mechanism is independent of the control of rotation of the patient support apparatus 310 by the rotation mechanism. Both movements are controllable by one or more processors.

The height adjustment mechanism is configured to control a height of the patient support apparatus 310 above the floor of the treatment room. It follows that the height adjustment mechanism is configured to control a height of the patient support apparatus 310 above the base 328 of the support structure 320. The height adjustment mechanism thereby also increases the height of the principal rotation axis (as defined by the principal coupling point/the first supporting leg coupling point 511). For example, with reference to FIG. 5a, it can be seen that clockwise rotation of the upper supporting leg 322 about the axis defined by the second (supporting leg) coupling point 512 increases the height of the patent support apparatus 310 and the first (supporting leg) coupling point 511.

In other words, the patient support apparatus 310 is configured to rotate, with respect to the support structure 320, about a principal axis (e.g. a pitch axis). The rotation mechanism controls this rotation. The height adjustment mechanism controls the height of the principal axis. These adjustments can be controlled together in order to define an 'effective' axis of rotation. For example, by rotating the patient support apparatus 310 about the pitch rotation axis and also increasing the height of the pitch rotation axis at the same time, in the reference frame of the treatment room the effect is that the patient support apparatus 310 rotates about an effective axis of rotation which does not align with the principal rotation axis defined by the point 511 at which the patient support apparatus 310 and the support structure 320 are coupled to one another. By controlling these degrees of freedom appropriately, the effective axis of rotation can be made to pass through the isocentre. By controlling pitch, yaw, and roll, it is possible to define the isocentre as an effective point of rotation about which the patient support surface can rotate.

Figure 7A:
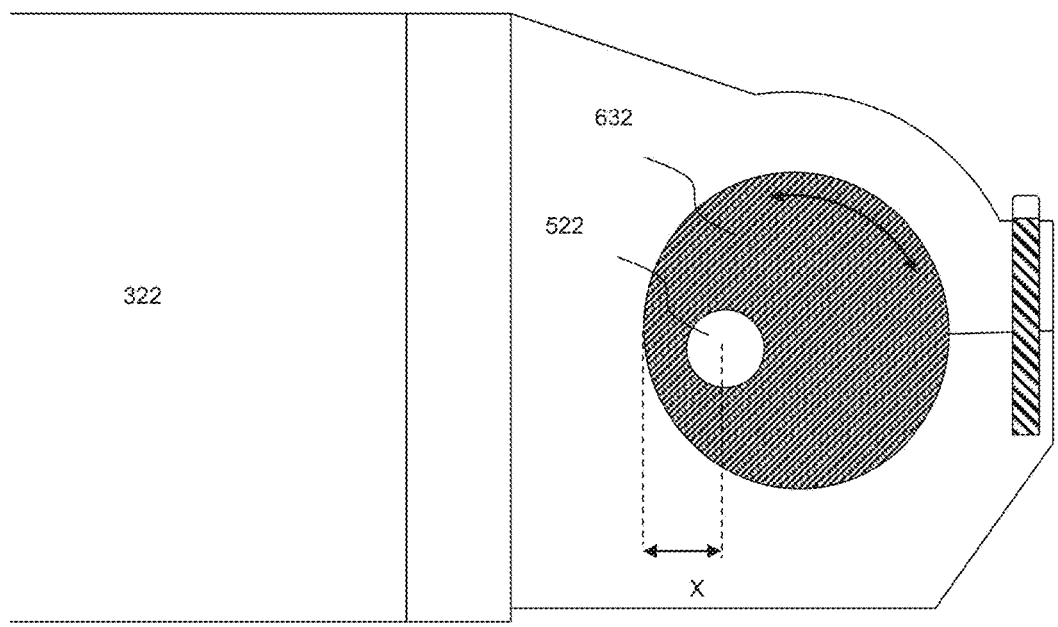
Figure 7B:
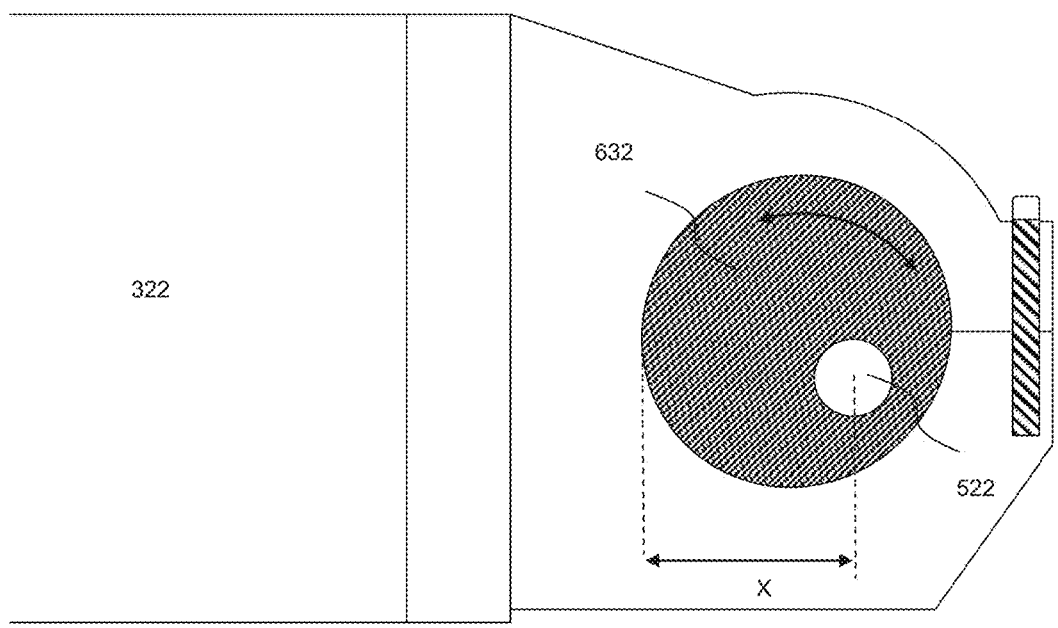

FIG. 6 depicts a close-up version of the rotation mechanism depicted in FIGS. 3a-c, 4a,b and 5a. FIGS. 7a and 7b show a cross-section through the joint which defines the second drive member coupling point 522.

The drive member 322 is rotationally coupled to the upper coupling element 325 at a first coupling point 521 and rotationally coupled the support element 324 at a second coupling point 522 as described above. The drive member 322 may thus rotate about a first axis (defined by the first coupling point 521) and a second axis (defined by the second coupling point 522). This second axis may be referred to as a 'common' axis of rotation as will be described below.

The actuation mechanism comprises a motor 612 configured to propel a drive nut 616 along a threaded shaft 618. The motor 612, drive nut 616 and threaded shaft 618 form part of a linear actuator arrangement. The linear actuator arrangement may be a ball screw actuator, the functionality of which will be understood by the skilled person. The linear actuator arrangement further comprises a housing 614. The housing 614 is rotationally coupled to the drive member 322. The housing 614 comprises one or more spindles 615 which fit into corresponding apertures within spindle holders 624 fixedly attached to the drive member 322. This arrangement allows the linear actuator arrangement, including the motor 310 and threaded drive shaft 618, to rotate with respect to the drive member 322 about an axis defined by the spindle(s) 615 and spindle holder(s) 624. This rotation axis is perpendicular to the longitudinal axis of the drive member 322 and parallel with each of the rotational axes described above in relation to the principal axis and the various coupling points.

The rotation mechanism further comprises a motion converter 632. The motion converter 632 is rotationally coupled to the drive member 322, and to the support element 324, at the second (drive member) coupling point 522. Thus, both the drive member 322 and the motion converter 632 may rotate with respect to the support element 324 about a common axis of rotation defined by the second drive member coupling point 522. The motion converter 632 is configured to convert linear motion of the linear actuator, and in particular the linear motion of the drive nut 616 along the threaded shaft 618, into rotatory motion about this common axis of rotation.

The actuation mechanism comprises a linear actuator coupled to the motion converter such that actuation of the linear actuator causes the motion converter to rotate about the axle. To achieve this conversion, the motion converter 632 comprises a crank arm 634, or link arm, which is coupled to the drive nut 616. The crank arm 634 is rotationally coupled to the drive nut 616 by virtue of one or spindles extending out from the drive nut 616, which fit in corresponding apertures (or spindle holders) in the crank arm 634. The various features are arranged and configured such that linear movement of the drive nut 616, controlled by the motor 612, causes rotation of the motion converter 632 about the common axis of rotation. The linear actuator is coupled to the crank arm of the motion converter such that actuation of the linear actuator causes the motion converter to rotate about the axle.

The motion converter 632 passes through an aperture in the drive member 322. The aperture extends in a direction defined by the longitudinal axis of the drive member, and may be circular in shape. The motion converter 632 is mounted eccentrically with respect to the common axis of rotation. In the implementation depicted in FIG. 6, the support element 324 comprises an axle at 522 which defines the location of the common axis of rotation, and the motion converter 532 is mounted eccentrically with respect to this axle 522. This mounting is shown in detail in FIGS. 7a and 7b. As will be appreciated from the accompanying description of these figures, the motion converter 532 is eccentrically mounted with respect to the axle such that rotation of the motion converter 532 about the axle causes linear movement of the drive member 322 in the manner discussed elsewhere herein.

FIGS. 7a and 7b depict the joint at which the motion converter 632 and the drive member 322 are coupled to the fixed axle of the support element 324. Both the drive member 322 and the motion converter 632 may rotate about this axle and thus the drive member 322 and the motion converter 632 share a common axis of rotation. Rotation of the motion converter 632 about this axis is controlled by the motor 612, via its control of the movement of the drive nut 616 along the threaded shaft 618.

As is described elsewhere herein, the rotation mechanism is configured to adjust a distance between the two rotational coupling points of the drive member 322. This can be achieved by adjusting the distance X depicted in FIGS. 7a and 7b. FIG. 7a shows the distance X toward, or at, its minimum. FIG. 7b shows the distance X toward, or at, its maximum. The position of the axle defines the second, or lower, coupling point 522 of the drive member 322. By rotating the motion converter 632 about the common axis it shares with the drive member 322, the amount of the motion converter 632 which is interposed between the first and second coupling point of the drive member 322 is adjusted. This is achieved by virtue of the eccentric mounting of the motion converter 632 with respect to the axis at 522.

This particular implementation of the rotation mechanism is advantageous. The motion converter 632 is eccentrically mounted with respect to a fixed axle of the supporting structure 320, and the drive member 522 is also rotationally mounted to the axle to define a rotation axis common to both the drive member 322 and the motion converter 632. This arrangement allows the linear movement of the drive member 322 along its longitudinal length (which movement controls the rotation of the patient support apparatus) to be controlled via a linear actuator arrangement; however, crucially, the full load of the patient support apparatus is not born by the linear actuator arrangement. Thus, a more stable arrangement is provided which is less prone to damage and issues causes by mechanical wear.

Figure 8A:
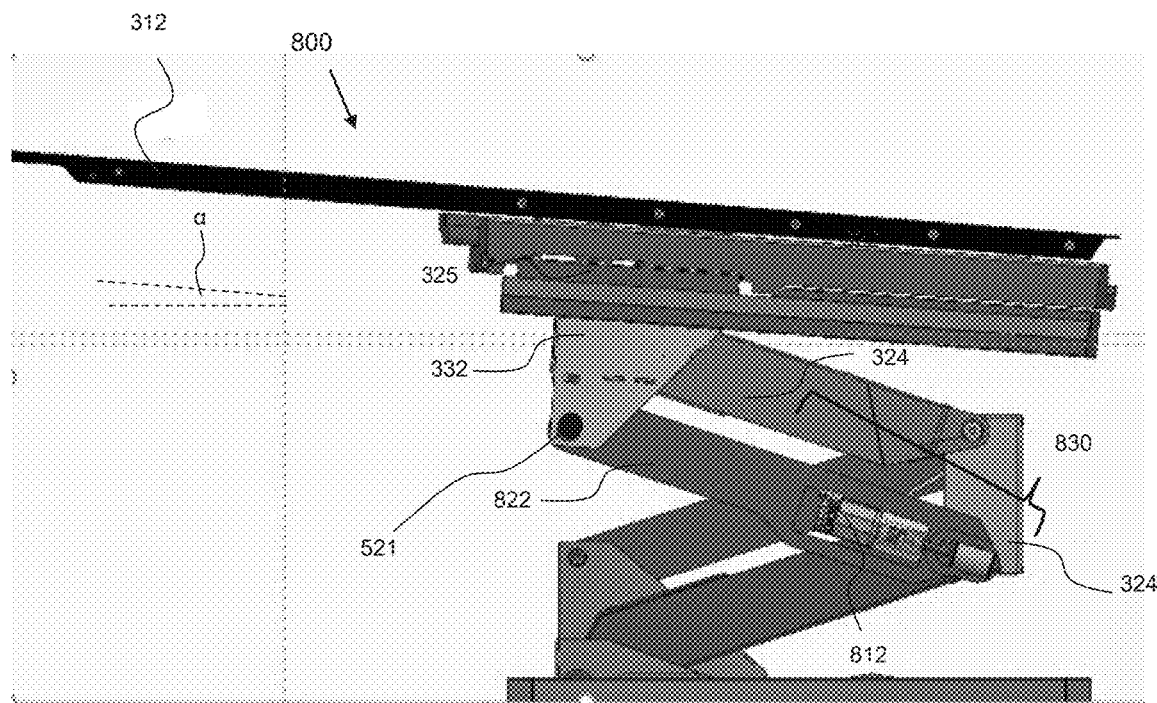
FIGS. 8a, 8b depict a patient positioning apparatus at different tilt angles, according to a second implementation of the present disclosure.
Figure 8B:
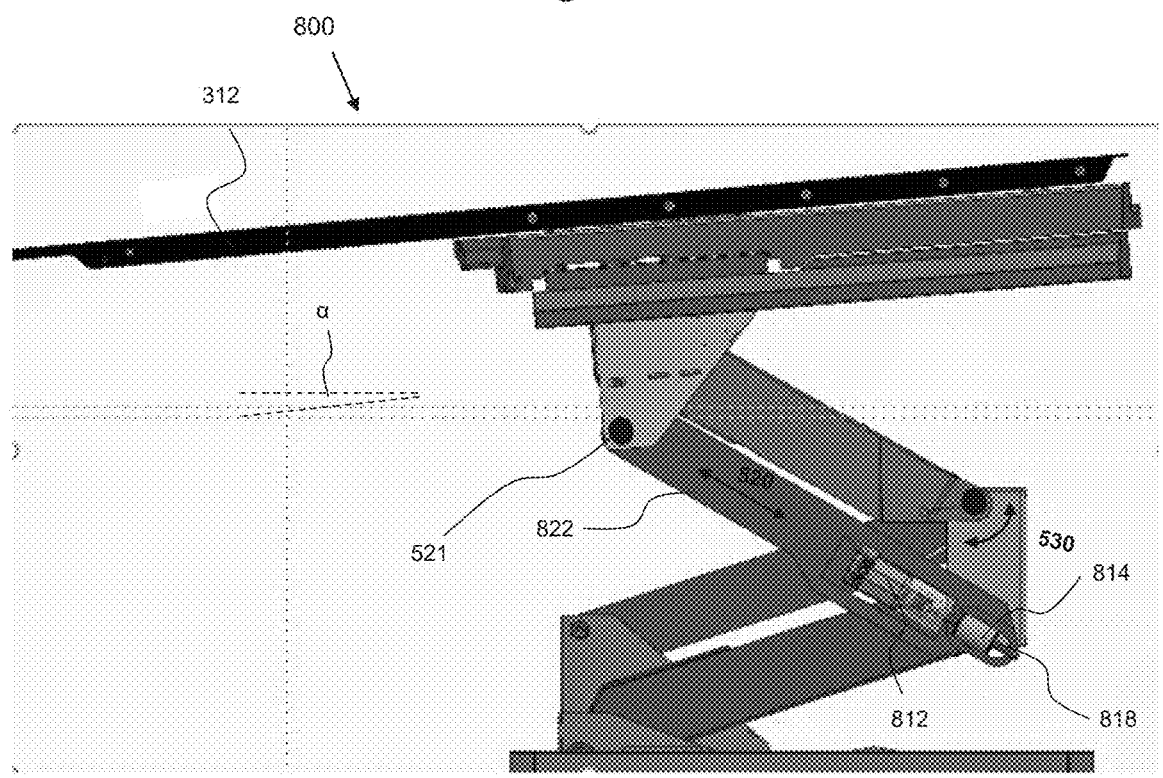

FIGS. 8a and 8b depict a patient positioning apparatus 800 comprising an alternative implementation of the rotation mechanism. Other than the rotation mechanism, the arrangement 800 of FIGS. 8a and 8b is similar to the arrangement 300 depicted in FIGS. 3-c and 4a,b, and like reference numerals are used to refer to like features. FIG. 8a depicts the apparatus 800 at or toward its maximum positive tilt angle α, and FIG. 8b depicts the apparatus 800 at or toward its maximum negative tilt angle α. FIGS. 7a and 7b show a cross-section through the joint which defines the second drive member coupling point 522 in this implementation. The actuation mechanism is not shown in FIGS. 7a and 7b.

The rotation mechanism comprises a drive member 822 and an actuation mechanism 830. The actuation mechanism 830 achieves the same effect as rotation mechanism 330 described above. In particular, the actuation mechanism 880 is configured to move the drive member 822 so as to impart a force to an underside of the patient support apparatus and thus tilt the patient support apparatus with respect to the support structure. The actuation mechanism 830 comprises a motor 812, a drive nut 814, and a threaded shaft 818. The actuation mechanism 830 may be a high load ball screw actuator or roller screw actuator, or may be a suitable high load hydraulic actuator.

The drive member 822 comprises an aperture 902. The aperture 902 extends in a direction defined by the longitudinal axis of the drive member 822. The motor 812, drive nut 814, and threaded shaft 818 are attached to, and may be integral with, the drive member 822. The motor 812 is rigidly affixed to the drive member 822 and is configured to move with the drive member 822. The threaded shaft 818 extends parallel with the aperture 902, i.e. in a direction parallel with the longitudinal axis of the drive member 822. The threaded shaft 818 may extend into the aperture 902. The threaded shaft 818, drive nut 814 are not shown in FIGS. 9a, 9b.

An axle extends from the support element 324 to define the location of the lower (or second) drive member coupling point 522. The axle extends into the aperture 902 and is rotationally coupled to the drive nut 814 to define an axis about which the drive nut 814, and hence drive member 822, may rotate with respect to the support element 324. The drive nut 814 may also be referred to as a drive member or drive element.

The drive element 814 is rotationally coupled to the support structure, but has no translatory of degrees of freedom with respect to the support element 324. The drive element 814 is rotationally attached to an axle which cannot move with respect to the support structure. The motor 812 is configured to control the position of the drive nut 814 along the threaded shaft 818. Because the axle is coupled to the drive nut 814 in or though aperture 902, actuating the motor 812 has the effect of controlling the location of the axle in the aperture 902. Actuating the motor 812 in a particular direction has the effect of pushing the motor 812, and with it the drive member 822, away from the drive nut 814. Actuating the motor 812 in the opposite direction has the effect of pulling the motor 812, and with it the drive member 822, toward the drive nut 814.

Figure 9A:
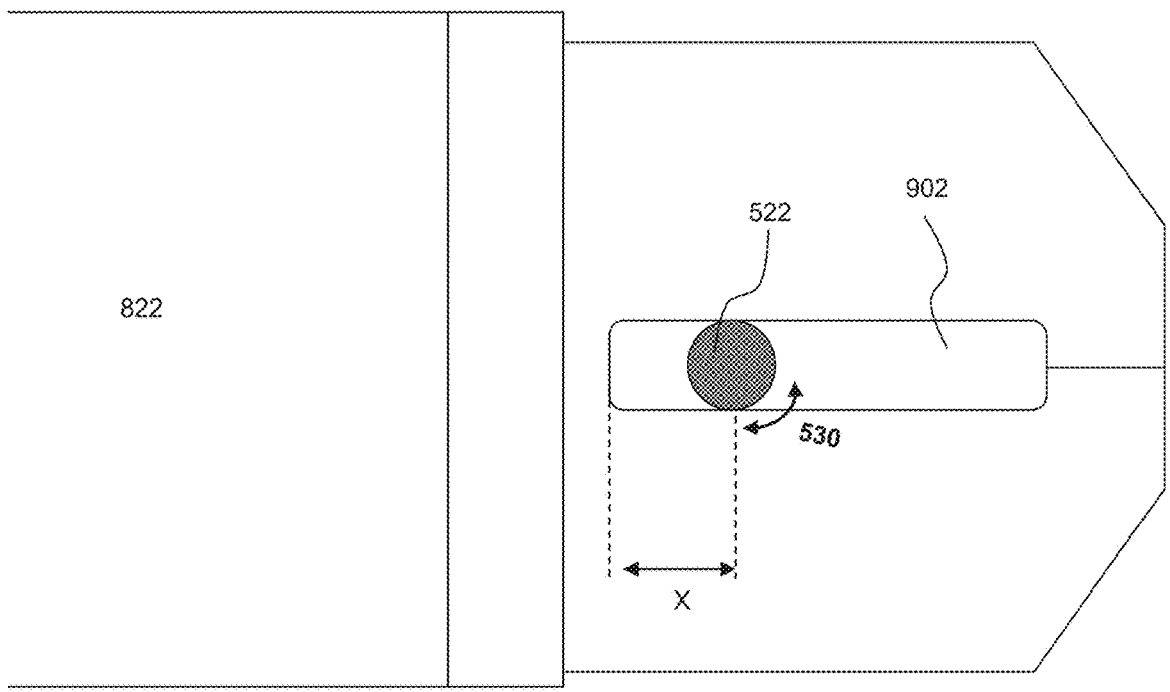
FIGS. 9a, 9b depict a cross section through a drive member of the rotation mechanism depicted in FIGS. 8a and 8b.
Figure 9B:
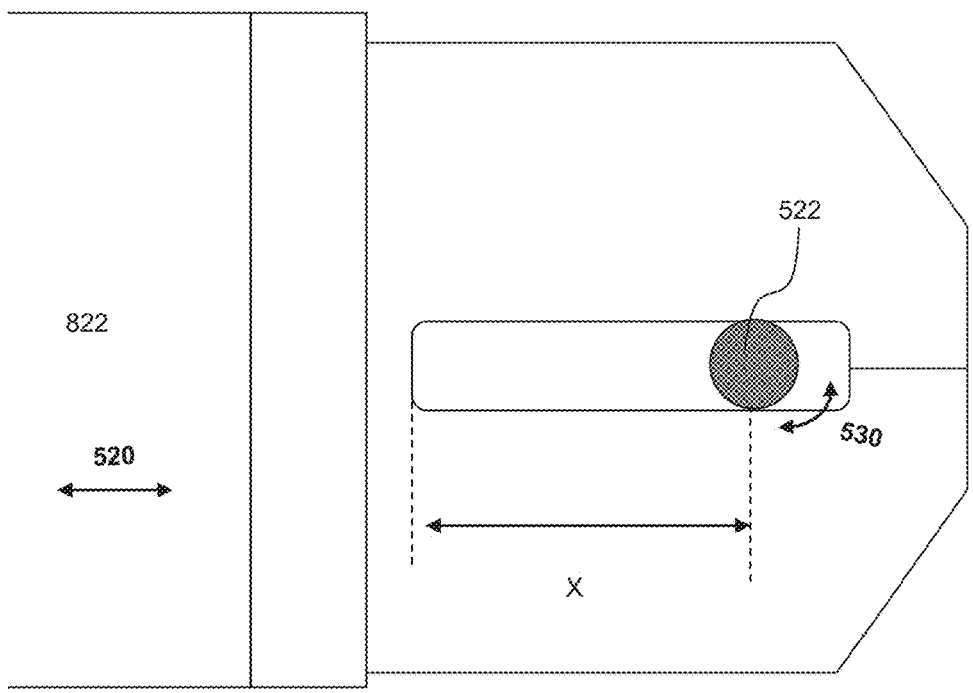

This functionality can be appreciated upon inspection of FIGS. 9a and 9b. The actuation mechanism is not shown in these figures, but is configured to control the movement of the axle at 522 within the elongated aperture 902. Therefore, the actuation mechanism is configured to control an adjustable distance, X, in a manner similar to the actuation mechanism 530 depicted in FIGS. 7a, 7b.

As the actuation mechanism 330 adjusts the distance between the first and second coupling point, the distance between the first coupling point and the support element 324 is also adjusted. By increasing the distance between the first and second coupling points, the first coupling point, and thus the coupling element, is pushed away from the support element 324 of the support structure 320. Conversely, by reducing the distance between the first and second coupling points, the first coupling point, and thus the coupling element 325, are pulled toward the support element 324 of the support structure 320.

As with actuation mechanism 330, the actuation mechanism 830 is configured to adjust the distance between the first and second drive member coupling point. Adjusting this distance in one of the two possible directions moves the drive member 822 in that same direction. By virtue of this arrangement, the rotation mechanism is configured to impart a force, via the drive member 822, to an underside of the patient support apparatus to thereby rotate the patient support apparatus with respect to the support structure.

Still further alternatives of the rotation mechanism are possible. In a simple alternative embodiment to the implementations described above, the drive member may have an adjustable length. The actuation mechanism is configured to adjust this length in order to impart a force to an underside of the patient support apparatus. This may be achieved using a telescoping linear actuator. For example, a first, radially outer element of the drive member may be coupled to one of the support element or the coupling element, and a second, radially inner element of the drive member may be coupled to the other of the support element or the coupling element. The actuation mechanism is configured to control the degree to which the inner element extends out from the outer element in a manner that will be known to the skilled person, who will be familiar with different forms of linear actuators. Thus, by controlling the length of the drive member, the distance between the first, upper drive member coupling point and the second, lower coupling point of the drive member can be controlled in a manner similar to that described above. Control of this distance allows a force to be imparted to the underside of the patient support apparatus in order to tilt the patient support apparatus in the manner described elsewhere herein.

The patient positioning apparatus may further comprise a swivel mechanism, which is embeddable within a floor of a treatment room, and which is configured to rotate the patient positioning apparatus with respect to the treatment room. This may be described as a yaw rotation. This mechanism is in accordance with known mechanisms and need not be discussed further herein.

It is worth noting that, while the implementations described in detail herein control a tilt in the form of a pitch rotation, the skilled person will appreciate that the presently disclosed rotation mechanism may effect rotation about any of a number of different axes, and in particular may control a roll rotation if the patient support apparatus is correctly oriented with respect to the support structure.

In some implementations, one or more inclinometers are used to measure the position of the patient support surface. In some examples, a dual axis inclinometer is placed at an appropriate location in order to measure the pitch and roll angles of the patient support surface. On one of its axes, the inclinometer measures an absolute value for the pitch angle of the patient support surface, and on the other of its axes, the inclinometer measures an absolute value for the roll angle. In some examples, an additional inclinometer can be used to measure the yaw, or heading, rotation of the patient support surface as an absolute angle value. Alternatively, a single electronic compass, or a three axis inclinometer, may be used to provide a measure of the absolute angle of pitch, roll, and yaw of the patient support surface. Whether one or more inclinometers or electronic compasses are used, multiple alternative or complementary mounting locations are possible. In some examples, a single inclinometer or electronic compass is mounted to the patient support surface. In some examples, a single inclinometer or electronic compass is mounted directly under the patient support surface. In examples in which multiple inclinometers are used, one inclinometer, or electronic compass, may be mounted to the side of the patient support surface and another mounted directly under the treatment table. Any mounting location which allows the determination of the desired angle may be used. Whichever configuration is used, the inclinometer is oriented appropriately to measure the angle desired to be measured, for example, by orienting an axis of the inclinometer to measure the roll angle of the table.

Known techniques measure the movements of patient support systems using linear or rotation encoders, which provide a value of the mechanical movement required for a particular roll and pitch. However, such measurements are influenced by factors such as mechanical tolerances and do not measure roll and pitch directly. Advantageously, an inclinometer measures the absolute value of the roll, pitch, and/or yaw, providing the actual position of the table even in instances of bending or deformation, such as that due to the presence of a patient.

Furthermore, by using inclinometers mounted to the patient support surface, the movement of the table can be measured at the table itself, which is more precise than a solution where the pitch is measured at the pitch articulation and control mechanism. Furthermore, obtaining an absolute measurement means that the horizontal calibration of the table can be set at installation by using the inclinometer measurements.

A general aim of the present disclosure is to provide a space-efficient and compact apparatus. By providing a rotation mechanism in the manner disclosed herein which is attached to, and supported by, the support structure, a number of benefits are provided. Mechanical 'pinch points' no longer limit the maximum degree of tilt, and the need for a large separation between a base plate and a patient support surface is removed. Thus, the hop-on height is advantageously reduced. The attachment of the rotation mechanism to support structure which is configured to support the patient support apparatus, e.g. in the support legs of the apparatus, means that the rotation mechanism and in particular its actuation mechanism is easier to access, service and repair. Linear movement of the patient support surface with respect to a patient support base is facilitated as the entire patient support apparatus is lighter and less bulky, and the need to translate not only the patient support apparatus but also the rotation mechanism as part of this movement is removed.

In some implementations, a tilting mechanism may be provided between the patient support surface and the patient support base which is configured to tilt the patient support surface with respect to the patient support base about a tilting axis (e.g. a roll rotation axis). Such a tilting mechanism can be simplified and made more compact, hence reducing the hop-on height, by removing the need for this tilt mechanism to provide a tilt about both a pitch and roll axis. By providing a rotation mechanism in the manner disclosed herein which is attached to, and supported by, the support structure, and which is configured to provide (for example) rotation about a pitch rotation axis, the tilting mechanism positioned between the patient support surface and the patient support base need only provide tilting about the roll axis. This means that both rotational degrees of freedom (pitch and roll) may be provided independently, while allowing the tilting mechanism placed between the patient support surface and the patient support base to be simplified and made more compact.

Having the support structure support the weight of the patient support apparatus, with a separate rotation mechanism which controls rotation with respect to that support structure, means that the rotation mechanism itself need not directly support a heavy load. This reduces mechanical wear and tear, reduces chances of breakdown, and increases the longevity of the apparatus.

Sensor Arrangement(s)

Also disclosed herein is a patient positioning device which comprises a tiltable patient support apparatus and a sensor arrangement configured to determine a degree of tilt. Adjusting the position of a patient using a patient positioning apparatus or device is common in various fields of medicine. For example, the patient may be tilted prior to or during radiotherapy treatment in order to adjust the position of the patient with respect to a source of therapeutic radiation, and thereby to adjust the dose distribution in the patient's body. For example, a treatment plan may call for the adjustment of the patient via tilting the support surface in order to reduce the dose applied to a particular region of healthy tissue.

For safety reasons, it is very important to be able to determine the position of the patient prior to and during treatment. Actuator arrangements may be used to adjust the height of a patent support surface, or the degree to which the patient is tilted, and the traditional way to measure the height and/or tilt is to place encoders on all the motors and joints of the patient positioning device. The signals from each of these encoders can be used to indirectly measure the angle and height of the patient table. This prior process requires the processing of several measurements, through the mechanical structure, to finally reach the resulting tilt angle. Every step in the determination introduces inaccuracies, due to measurement errors and structural stiffness, that will add uncertainty to the result.

The present application seeks to address these and other disadvantages in the prior art by providing a patient positioning device or apparatus comprising an improved sensor arrangement.

Disclosed herein is a patient positioning device which comprises a tiltable patient support apparatus and a sensor arrangement. The sensor arrangement comprises a processor and at least two sensors communicatively coupled to the processor. The sensors are spaced from one another, and each sensor is configured to measure a distance between an underside of the patient support apparatus and a respective fixed location. The sensors may be located at the fixed locations; for example, the sensors may be incorporated into a base of the patient positioning device such that the sensors measure a distance from the base to the underside of the patient support apparatus. Based on these signals, the processor can determine the degree of tilt of the patient support apparatus.

By measuring these distances directly, and along a line of sight of the sensors, the measurement of tilt is greatly simplified. It is possible to use a simple ratio of the measured distances in order to determine the degree of tilt. In this manner, fewer errors, for example due to sensor error margins and structural tolerances, are introduced to the measurement in comparison with prior techniques which measure the tilt using indirect measurements.

Ensuring the accuracy of the measured tilt angle is important. It has been found that a rotational error of 3° reduces coverage of a clinical target volume in brain tumors treated with intensity modulated radiotherapy from 99.3 to 97.0%. In other words, when the patient positioning device is used in conjunction with a radiotherapy device, improving the accuracy of the tilt measurement means also improves the accuracy and efficacy of radiotherapy treatment.

Figure 10:
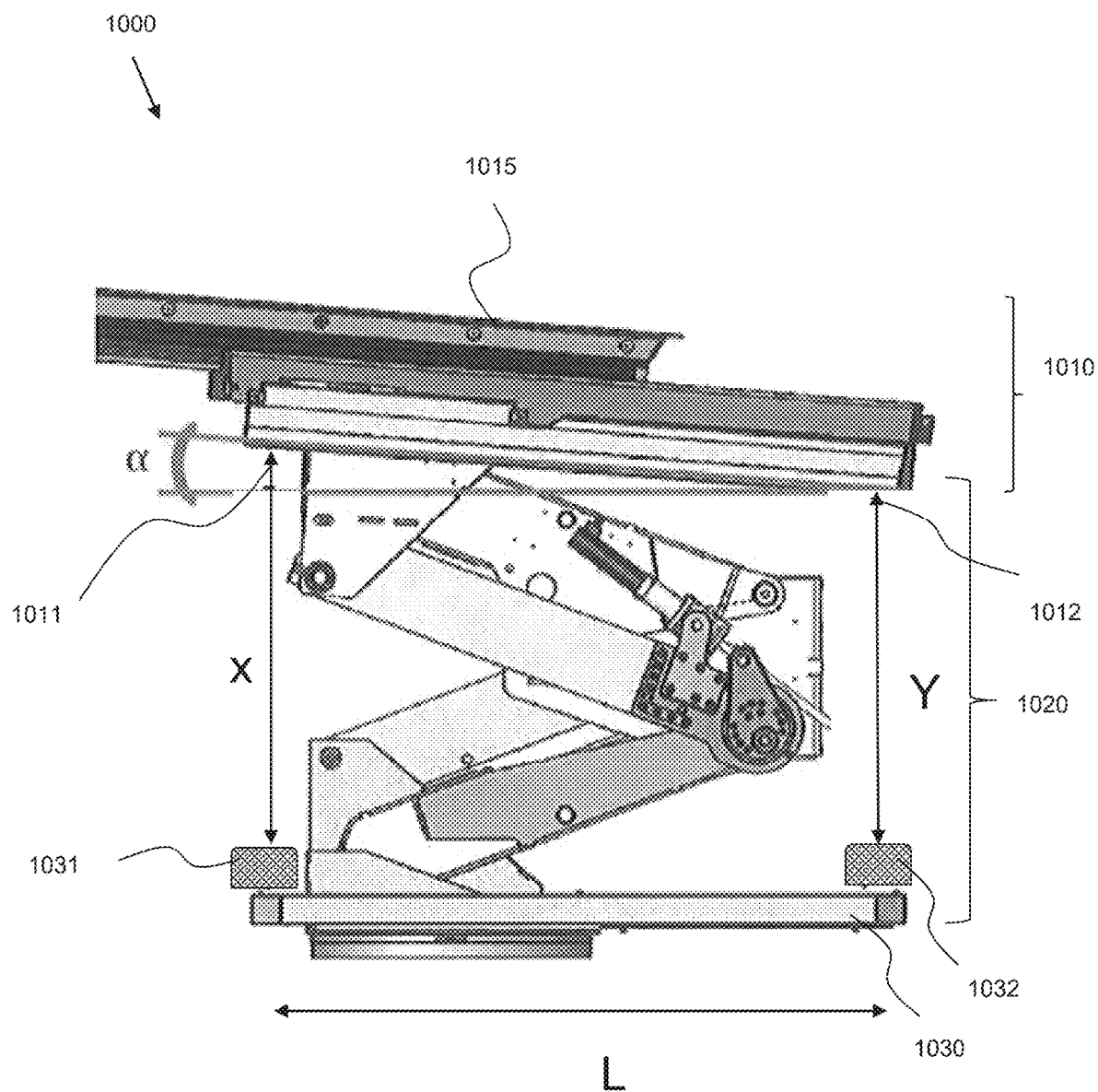
FIG. 10 depicts a patent positioning apparatus comprising a sensor arrangement according to a third implementation of the present disclosure.

FIG. 10 shows a patient positioning apparatus/device 1000 according to the present disclosure. The positioning device 1000 may be substantially as described elsewhere herein, or may take another form. The device 1000 comprises a patient support apparatus 1010 comprising a patient support surface 1015. The device 1000 further comprises a base 1030, and support structure 1020 to support the patient support apparatus 1010 above the base 1030. A patient may lie on the patient support surface 1015 when the patient positioning device 1000 is in use.

Figure 11:
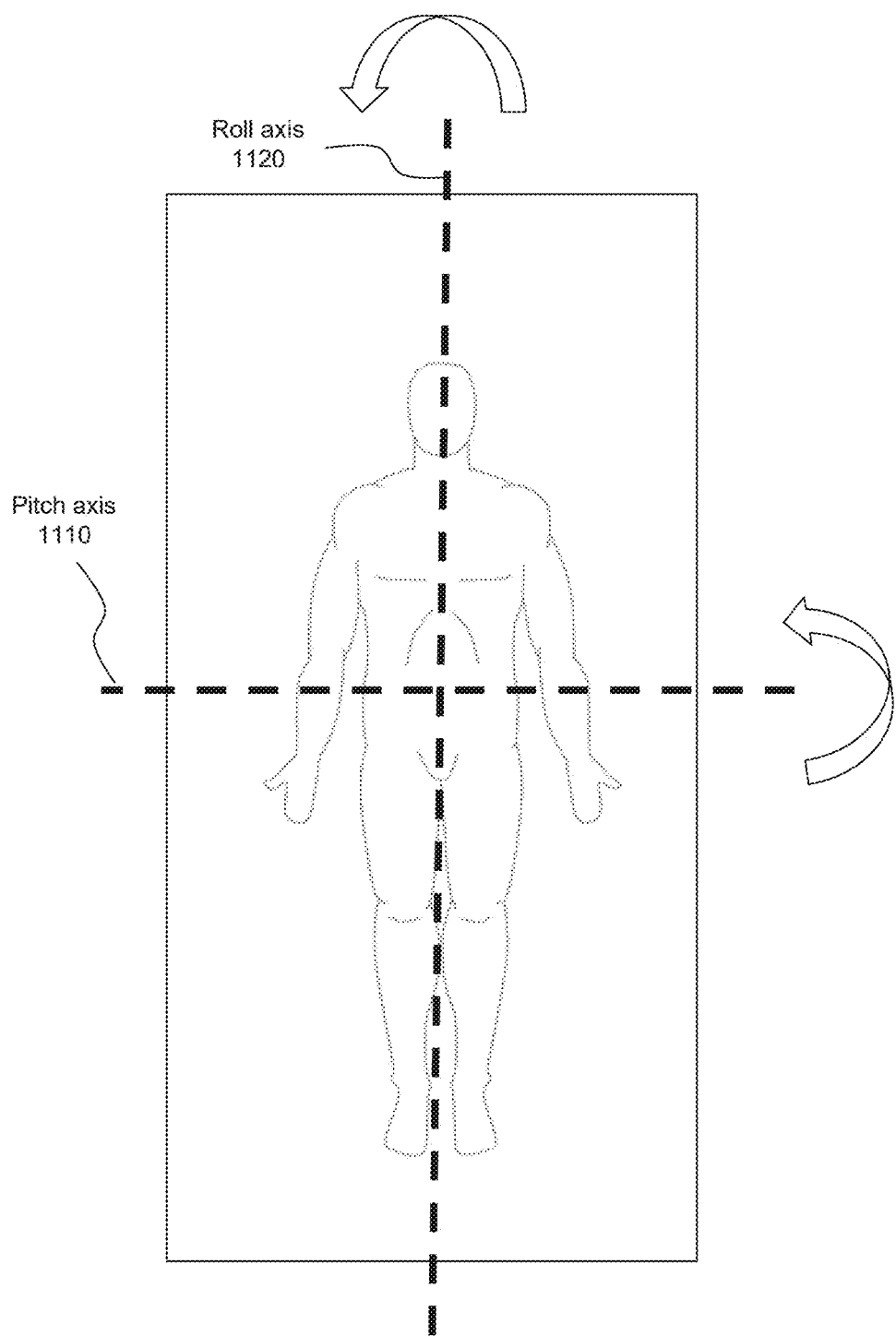
FIG. 11 depicts the pitch and roll axis of an exemplary patient support apparatus.

The device 1000 comprises a rotation mechanism, or system, which may take any appropriate form, for example the form described elsewhere herein. With reference to FIG. 11, the rotation system is configured to tilt the patient support apparatus 1010, and thereby the patient support surface 1010, about a pitch axis 1110. Alternatively or additionally, the rotation system may be configured to tilt the patient support apparatus 1010, and thereby the patient support surface 1015, about a roll axis 1120. The rotation system may therefore be configured to cause and control rotation of the patient support apparatus by one or both of pitch and roll. The rotation system may be comprised of separate pitching and rolling mechanisms. The exact form of the rotation mechanism is not important, and several implementations are envisaged.

The device 1000 further comprises a sensor arrangement. The sensor arrangement comprises a plurality of sensors. The plurality of sensors comprises at least a first sensor 1031 and a second sensor 1032. The sensor arrangement comprises a processor (not shown), and the first and second sensors 1031,1032 are communicatively coupled to the processor. The sensors 1031,1032 send signals to the processor, and based on these signals the processor is configured to determine a degree of tilt a of the patient support apparatus 1010.

The first sensor 1031 is configured to provide signals indicative of a first distance, X, between a first region 1011 of the underside of the patient support apparatus 1010 and a first fixed location underneath the patient support apparatus 1010. Similarly, the second sensor 1032 is configured to provide signals indicative of a second distance, Y, between a second region 1032 of the underside of the patient support apparatus 1010 and a second fixed location underneath the patient support apparatus 1010. Distances X,Y can be described as vertical distances.

The sensors produce signals indicative of the distances X,Y. The value of X can be derived from signals produced by the first sensor. For example, in the case of an optical sensor, the signals produce might relate to the intensity of light which has been reflected back from the underside of the patient positioning apparatus. The value of X can be derived by reference to calibration data, which in a simple form may be a look-up table relating light signal intensity to distance values.

Reference is made to fixed locations. In some implementations the base may be configured to swivel or rotate, thereby rotating the entire patient positioning device. In such an implementation, the term 'fixed location' or 'fixed position' means fixed with respect to the base, rather than fixed with respect to the treatment room.

In the implementation depicted in FIG. 10, the first sensor 1031 is located at the first fixed location such that the distance X is a distance between the first sensor 1031 and the first region 1031 of the underside of the patient support apparatus 1010. The second sensor 1032 is located at the second fixed location such that the distance Y is a distance between the second sensor 1032 and the second region 1032 of the underside of the patient support apparatus 1010.

The first and second fixed locations may be located substantially at, or on, a base 1030 of the patient positioning device 1000. In the implementation of FIG. 10, the sensors are positioned on the base 1030 of the device 1000 such that distances X, Y can be thought of as the distance between the regions 1011 and 1012, of the underside of the patient support apparatus 1010 and the base 1030, accounting for any systematic 'additional distance' introduced by the positioning of the sensors 1031, 1032, for example the height of the sensors 1031, 1032 above an upper surface of the base 1030.

The sensors 1031, 1032 may take many forms. For example, the sensors 1031, 1032 may be optical sensors such as optical distance sensors. Such sensors are known to the skilled person and typically make use of pulsed light. The strength of the returned signal from a target surface is indicative of the distance between the sensor and the target surface. Alternatively, the time taken for a beam to be reflected rom a target surface and return to the sensor may be used to determine the distance between the sensor and the target surface. In the implementation depicted in FIG. 10, the underside of the patient support apparatus 1010 represents the target surface for the optical sensors. However, equivalently, the sensors may be located on the underside of the patient support apparatus 1010, with the target surfaces being fixed positions underneath the support apparatus, for example fixed positions located on the base. The optical sensors may be used in conjunction with appropriately placed mirrors/light reflectors/targets to increase the efficiency of returned light, for example placed at the first and second region 1011, 1012, however mirrors/light reflectors are not required. The sensors may be triangulation laser sensors.

The sensors may be any suitable distance measurement sensors and may take other forms, and for example may take the form of draw string or draw wire sensors. A draw wire sensor comprises a main body and a wire rolls up like around a reel in the main body. The reel has a rotational encoder attached that counts the turns and hence the length of wire pulled out from the main body. The main body of the draw wire sensors may be coupled with the underside of the patient positioning apparatus 1010, with the wire extending downward toward a hook which is fixedly attached at one of the fixed locations. The displacement of the wire along the line joining a region of the underside of the patient positioning apparatus 1010 and the fixed location is then indicative of the distance between these points. Alternatively, the main body of the sensor may be positioned at the fixed position, with the opposing end of the wire fixedly attached to the underside of the patient positioning apparatus 1010. In other words, the string may be attached to the tilting surface with the sensor body attached to the fixed base 1030.

Another type of sensor which may be used is a linear travel sensors. Linear travel sensors may comprise, for example, a ring that travels along a rod. The ring's linear motion along the rod can be converted into electrical signals.

The sensors, be they draw-string/draw-wire, optical, or another type of sensor, may undergo some for of calibration routine. The calibration will be standard in nature for the type of sensor used, for example to calibrate the sensors for their linearity error to make them as accurate as possible, and to set the readings which correspond to zero tilt angle and/or zero height. Such calibration is known to the skilled person.

As can be seen in the implementation depicted in FIG. 10, the sensors 1031,1032 are spaced from one another. The sensors in FIG. 10 are spaced from one another so as to enable the determination of a degree of tilt a in the form of a rotation about the pitch axis 1110. As can be seen in FIG. 10, the degree of pitch a may be defined as the degree to which the patient support apparatus 1010, and with it the patient support surface 1015, has been tilted about the pitch axis 1110. The degree of pitch a may be defined in multiple ways, though it is not necessarily important to define the angle in a particular way; the important thing is that the system is configured to determine a change in angle α between different tilt positions. In an implementation, the degree of pitch a can be described as the angle which the patient support surface 1015 makes with a horizontal plane, or equivalently the angle which the patient support surface 1015 makes with the floor of the treatment room. α may also be referred to as the pitch angle.

The first and second fixed locations are separated by a separation distance L. When the sensor arrangement is configured to measure a pitch angle α, the separation distance L extends parallel to the roll rotation axis 1120. In other words, the first and second fixed locations are separated by a separation distance L along an axis parallel to the roll axis 1120. In the implementation depicted in FIG. 10, the first sensor 1031 and second sensor 1032 are positioned directly underneath and aligned with the roll axis 1120.

The patient positioning apparatus 1015 can be thought of as having a major axis and a minor axis. At zero pitch tilt, the major axis is parallel with and may align with the roll axis 1120, and at zero roll tilt, the minor axis is parallel with and may align with the pitch axis 1110. The pitch angle α may be defined by an angle formed between the major axis of the patient positioning surface 1015 and the roll axis 1120. The roll angle β may be defined by an angle formed between the minor axis of the patient positioning surface 1015 and the pitch axis 1110. The discussions relating to axes and pitch/roll angles in relation to FIG. 11 apply similarly to all implementations discussed herein.

The first and second fixed locations are separated in a direction parallel with this major axis, measured when the patient positioning apparatus is at zero tilt, such that the processor is configured to determine, based on signals from the sensors, the degree of pitch of the patient support apparatus 1010.

Another way of describing the major axis of the patient positioning apparatus 1000 is as a length axis. Using this terminology, the patient positioning surface 1015 comprises a length defining, at zero tilt, a length axis. The length axis is parallel with and may align with the roll rotation axis 1120. As can be seen in FIG. 10 with reference to FIG. 11, the first and second fixed locations are separated in a direction along the length axis/major axis/roll axis by a distance L. In a specific implementation, L may be, for example, substantially 1 m.

The processor is configured to determine, based on signals from the sensors, the degree of pitch of the patient support apparatus 1010. The degree of pitch, i.e. the pitch angle α, can be calculated using the following formula:

$$\alpha = \tan^{-1}\left(\frac{X-Y}{L}\right).$$

It will be appreciated that the determination of the pitch angle α using this simple formula relies on significantly fewer factors than previous measurement techniques, and thus fewer errors are introduced into the calculation.

Accordingly, disclosed herein is a method of determining a degree of tilt of the patient support apparatus 1010. In its simplest form, the method comprises determining the degree of tilt of the patient support apparatus 1010 based on signals received from the sensors 1031, 1032. The method may comprise determining, or deriving, a first value based on signals received from the first sensor 1031, determining, or deriving, a second value based on signals received from the second sensor 1032, and determining the degree of tilt based on a ratio of the first and second value. The values may be the distances X and Y. If the sensors are not located the same distance from the underside of the patient support apparatus 1010 at zero tilt, e.g. if X≠Y when α=0, then the known height difference between the first fixed location and the second fixed location is incorporated into the calculation in order to calculate a.

This method can be embodied on a computer-readable medium, which may be a non-transitory computer medium, which comprises computer executable instructions which, when performed by the processor, cause the processor to carry out the method.

The sensors in FIG. 10 are separated along a length axis of the couch, or equivalently along the roll rotation axis of the couch. This allows the sensors to measure the pitch angle. However, the first 1031 and second sensor 1032 may instead be separated in a direction parallel with a width axis of the couch, or equivalently along the pitch rotation axis of the couch. This can also be thought of as a separation in a direction parallel with the minor axis of the patient positioning apparatus 1000. This allows the sensors to measure the degree of roll, or roll angle, of the patient support apparatus 1010.

In other words, the patient positioning surface may comprise a width defining, at zero tilt, a width axis. This width axis is parallel or else aligns with the pitch rotation axis. By separating the first and second fixed locations along the width axis, the processor may use signals from the first and second sensors to determine the degree of roll of the patient support apparatus 1010.

Figure 13:
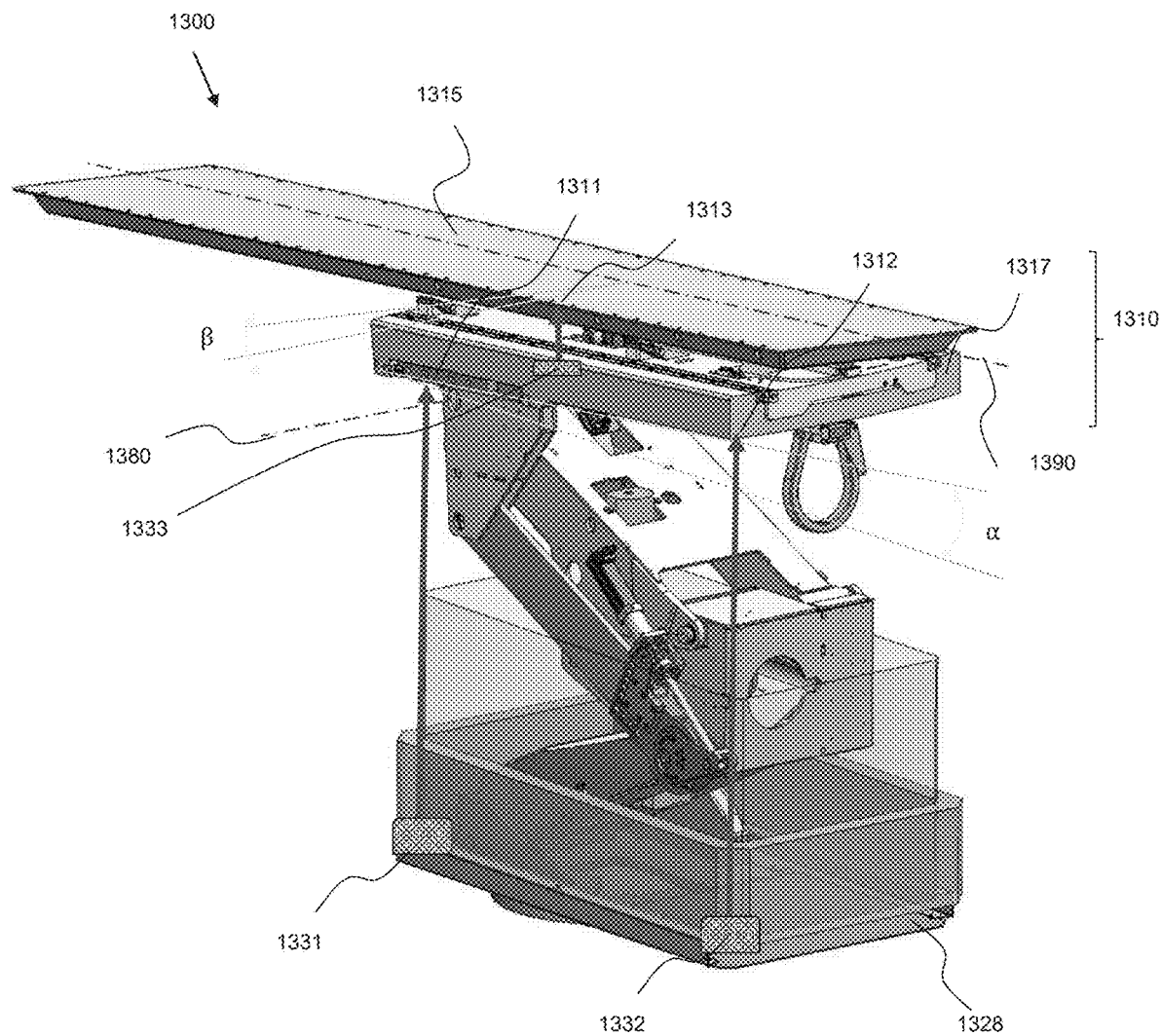
FIG. 13 depicts a sensing arrangement according to a fifth implementation of the present disclosure.

Generally speaking, by using just two sensors as depicted in FIG. 10, the height of the patient support apparatus base can be determined at any point along a line joining the first region 1011 and the second region 1012. However, in some implementations, the patient support base is configured to tilt in one degree of freedom (e.g. pitch), with the other tilting degrees of freedom of the support surface 1015 being effected by rotation mechanisms which do not cause tilting or movement of the patient support base. For example, the roll mechanism may be incorporated into the patient support surface and may effect roll tilting of the patient support surface 1015 with respect to the patient support base (such an implementation is depicted in FIG. 13). In such an implementation, in which the regions of the underside of the patient support base can only rotate about one tilting axis, it is possible to determine the height of any region of the underside of the patient support base using just two sensors In implementations in which the tilting of the patient support base is not limited to one degree of freedom, to ensure the height of the centre of the patient support apparatus can be determined, the sensors may be placed such that the centre point of the patient support apparatus 1010 lies along, or above, this line.

Figure 12A:
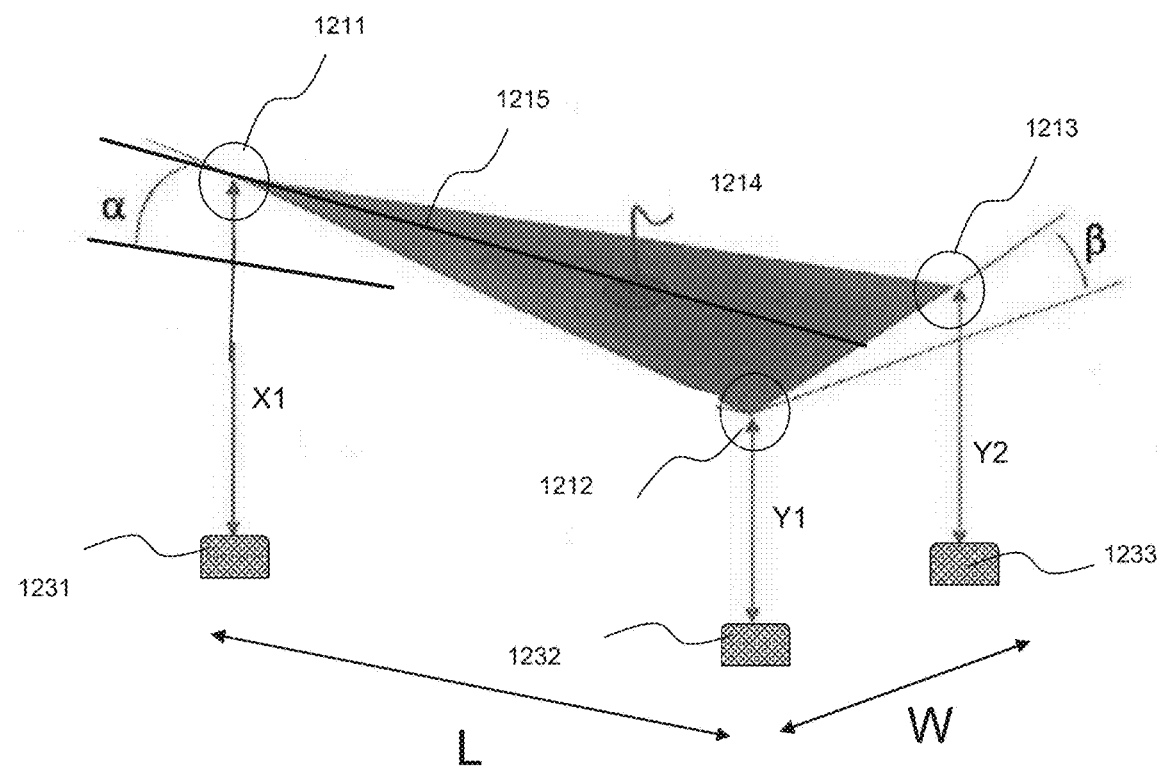
FIG. 12 depicts a sensing arrangement according to a fourth implementation of the present disclosure.
Figure 12B:
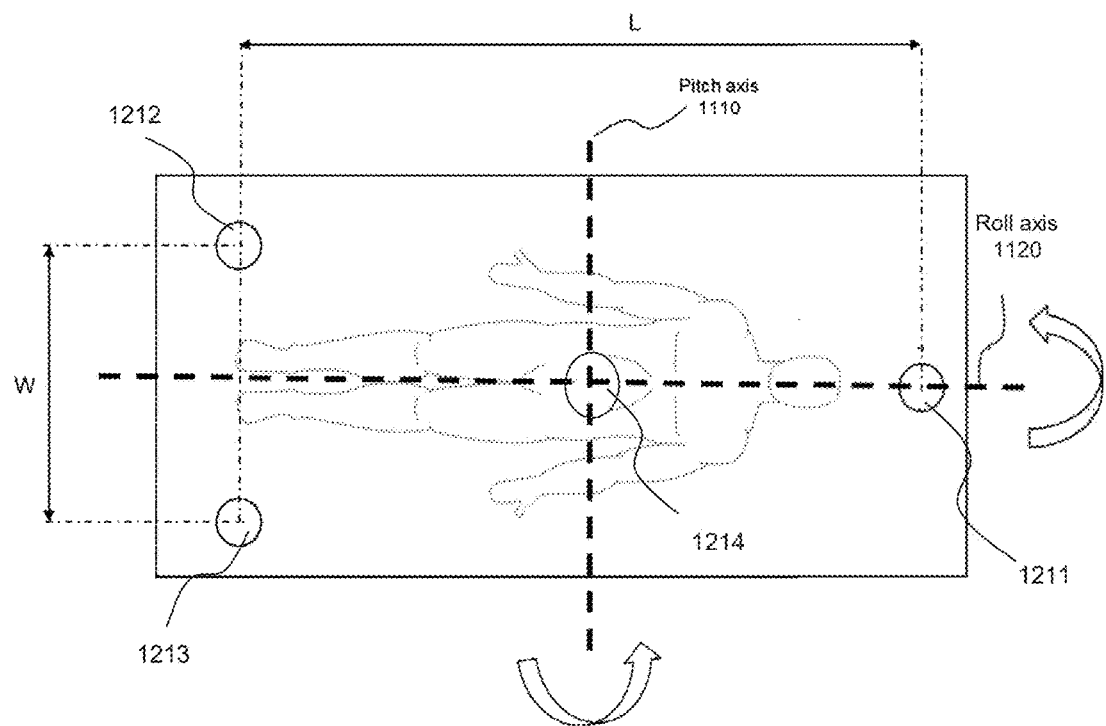

Another implementation of the present disclosure is depicted in FIGS. 12a and 12b. FIG. 12a shows a plane 1215 which can be defined using signals from a plurality of sensors. FIG. 12b is a view of a patient positioning apparatus from above and shows the patient support surface supporting a patient. The positions of four regions of an underside of a patient support apparatus/patient support surface. The regions 1211, 1212,1213,1214 are located on the underside of the apparatus, i.e. on a lower side opposite an upper side of the patient support surface, though it will be appreciated that their positions can nevertheless be indicated in a top down view of the patient support apparatus in the manner shown in FIG. 12b. In FIG. 12b, the table is shown at zero tilt.

In this implementation, a first sensor 1231 is positioned at a first fixed location and is configured to provide signals to a processor which are indicative of a distance X1 between the first fixed location and a first region 1211 of the underside of the patient positioning apparatus. A second sensor 1232 is positioned at a second fixed location and is configured to provide signals to the processor which are indicative of a distance Y1 between the second fixed location and a second region 1212 of the underside of the patient positioning apparatus. The second fixed location is separated from the first fixed location by a distance L as measured in a direction parallel with the roll axis/length axis of the patient support apparatus in the manner shown in FIG. 12b. A third sensor 1233 is positioned at a third fixed location and is configured to provide signals indicative of a distance Y2 between the third fixed location and a third region 1213 of the underside of the patient positioning apparatus. The third fixed location is separated from the second fixed location by a distance W as measured in a direction parallel with the pitch axis/width axis of the patient support apparatus. The first region 1211, second region 1212 and third region 1213 define a plane 1215 which describes the position in space of the patient support apparatus.

By arranging a plurality of sensors in the manner described with respect to FIGS. 12a and 12b, the degree of tilt of the patient support apparatus in the form of both pitch and roll can be determined. In FIG. 12a, the degree of pitch, i.e. the pitch angle, is denoted by a. The degree of roll, i.e. the roll angle, is denoted by 3. The processor is configured to determine, based on signals from the first, second and third sensors, the degree of pitch and the degree of roll of the patient support apparatus 1010. Processing performed by the processor may make use of appropriate and simple formulae, and in particular the processing may make use of relatively simple trigonometric calculations. In simple summary, the sensors allow you to measure the sides of a triangle, and compare with the known sides of the triangle from which is it possible to calculate an angle of interest. It will be understood that these calculations can be adjusted depending on the angles of interest and depending on the placement of the sensors. For example:

$$\alpha = \tan^{-1}\left(\frac{X1 - \left(\frac{Y1 + Y2}{2}\right)}{L}\right)$$

$$\beta = \tan^{-1}\left(\frac{Y2 - Y1}{W}\right)$$

In this implementation, the processor may be further configured to determine the height of the patient support surface, for example via determining the height of a fourth region of the underside of the patient support surface.

The height of the patient support apparatus 1010 can be determined using the distance information provided by each of the first, second, and third sensors. If height is defined as the distance between an underside of the patient support surface and the base, then if the fixed locations are located at the base of the patient positioning device, the distances measured by the sensors are height measurements. For example, in the implementations depicted in FIGS. 10 and 12a, 12b, the sensors form part of, and/or are embedded within, the base of the patient positioning device. With reference to the distances depicted in FIG. 12a, distance X1 can be thought of as the height of the first region 1031, Y1 can be thought of as the height of the second region 1032 and Y2 can be thought of as the height of the third region.

The distance/height information, in conjunction with knowledge of the relative positions of the sensors/fixed locations, can be used to define a co-ordinate in space for each of the three different regions of the underside of the patient support apparatus 1010. The three co-ordinates define a plane which describes the position in space of the patient support apparatus 1010. Using simple geometry, the co-ordinates, and thus height, of any point on the plane can be determined. In this way, the height of a fourth region of the underside of the patient support surface can be determined based on the distances measured by the three sensors.

The height may be defined in a number of ways, for example the distance between the fourth region 1214 and the base, or the floor of the treatment room. The desired height value may relate to the height of the centre of the patient support apparatus, and therefore the fourth region 1214 may be a central region of the patient support apparatus. The height of any point on the plane 1215 formed by the three measurements X1, Y1, and Y2 can be determined.

In another implementation (not shown), the patient support apparatus may be configured to rotate about a yaw axis that extends into the plane of the diagram shown in FIG. 12b. To measure a yaw angle, a sensor is provided which is tilted, or else mounted horizontally, with respect to the patent support apparatus. This is in contrast with the sensors described thus far, which are vertically mounted. If the yaw axis of rotation is fixed, one horizontally oriented sensor may be configured to determine the yaw rotation. Reading the increase in distance gives the side of the triangle from which the yaw angle can be calculated in a manner similar to that described above. If the patient support surface is configured to provide a horizontal displacement of the apparatus and the yaw axis, a second horizontally mounted sensor is provided to distinguish between what is a side movement and what is a rotation. These sensors sit outside the patient positioning system on a fixed surface relative to the treatment room. The same principles described above can be employed, though with horizontal rather than vertical measurements.

FIG. 13 depicts a patient positioning apparatus 1300. The patient positioning apparatus 1300 depicted is similar in form and functionality to the patient positioning apparatuses described elsewhere herein, and in particular the pitch rotation mechanism takes the form depicted in any of FIGS. 3a-7b. However, it will be appreciated from the following description that the pitch rotation mechanism may take any suitable form. The patient positioning apparatus 1300 also comprises a roll rotation mechanism incorporated into the patient support apparatus 1310.

The patient positioning apparatus comprises a patient support surface 1315 configured to rotate about a roll axis 1390 with respect to a patient support base or base structure 1317. This rotation is controlled by a rotation mechanism positioned between the patient support surface 1315 and the patient support base structure 1317.

The patient positioning apparatus further comprises a rotation mechanism, which may be similar in form to that described above in relation to FIGS. 3a-7b, configured to rotate the patient positioning apparatus about 1310 about a pitch rotation axis 1380 with respect to a positioning apparatus base or base structure 1328. This rotation is controlled by a rotation mechanism positioned between the patient support apparatus 1310, and in particular the patient support base or base structure 1317, and the base 1328. In this implementation the mechanical axes of pitch 1380 and roll 1390 are "stacked", and/or positioned in different layers, with respect to one another. In other words, these rotational axes are at different heights.

A first sensor 1331 and a second sensor 1332 are positioned to measure a height of a first region 1311 of the underside of the patient support base 1317, a height of a second region 1312 of the underside of the patient support base 1317, and determine a pitch angle α in the manner described above with respect to FIG. 10. These sensors placed in a lower 'layer', e.g. between the apparatus base 1328 and patient support base 1317, are used to calculate the height of the patient support apparatus and the pitch angle α.

The patient support base in the specific implementation shown is configured to be rotated about one axis of rotation with respect to the fixed location of the sensors 1331, 1332 positioned on the base 1328. This axis is the pitch rotation axis. The roll rotation mechanism is positioned between the patient support base and the patient support surface, and for example may take the form described with respect to FIGS. 14 to 16. This mechanism does not control movement of the patient support base, but instead controls movement of the patient support surface 1315 directly. The yaw rotation is controlled by the swivel mechanism, which rotates the entire device 1300, and with it the sensors 1331, 1332 and the patient support apparatus 1310. Because sensors 1331 and 1332 are measuring a distance to the underside of a base which itself is constrained to only rotate about one axis of rotation with respect to the sensors, it is possible to position the two sensors 1331, 1332 at any position underneath the patient support base and calculate the height of any position of the underside of the patient support base/apparatus. In particular, the two sensors can be moved anywhere in a parallel direction to the pitch rotation axis, and the sensors do not have to be positioned directly under the roll axis in order to determine the height of the central region of the patient support apparatus 1310. In other words, by restricting the mechanics it is possible to calculate the height anywhere on the underside of the patient support apparatus 1310 since this surface will always be parallel to pitch rotation axis 1380, which itself is always horizontal.

The apparatus further comprises a third sensor 1333 positioned between the patient support base 1317 and the patient support surface 1315. The third sensor is similar in form and functionally to those described elsewhere herein, and is configured to measure a distance from a third fixed location to a region 1313 of an underside of the patient support surface 1315. The third sensor 1333 may be positioned at the third fixed location. Signals received from the sensor 1333 positioned in this 'upper layer', i.e. between patient support base/base structure 1317 and patient support surface 1315, may be used to calculate the roll angle β. Accordingly, the third sensor 1333 may be referred to as a roll angle sensor or a roll rotation sensor. A single sensor in this layer may be used to determine the roll angle β by virtue of a simple calibration process which creates a mapping between measured height values and tilt angles.

A method of determining a degree of tilt of the patient support apparatus is also disclosed herein. The method comprises determining the degree of tilt of the patient support apparatus based on signals received from the sensors. A first value is calculated based on signals received from the first sensor, and a second value is calculated based on signals received from the second sensor. There may be some processing to account for any systematic height or distances, in particular if the first and second sensors are not placed in the same horizontal plane. The method comprises determining the degree of tilt based on a ratio of the first and second value. For implementations in which the patient support apparatus comprises a third sensor configured to provide signals indicative of a third distance between a third region of the underside of the patient support apparatus and a third fixed location underneath the patient support apparatus, the method may further comprise determining a third value based on signals received from the third sensor; determining the degree of pitch of the patient support apparatus based on the ratio of the first and second value, and determining the degree of roll of the patient support apparatus based on the ratio of the second and third value.

The method may be used with a patient support base structure and a patient support surface, where the patient support surface is tiltable about a roll rotation axis with respect to the base structure, and wherein the apparatus comprises a roll rotation sensor coupled to the processor and configured to provide signals indicative of a distance between a first region of the underside of the patient support surface and a fixed location between the patient support base structure and the patient support surface. In such an implementation, the method may also comprise determining a degree of pitch of the patient support apparatus based on signals received from the first and second sensors, and a degree of roll based on signals received from the roll rotation sensor.

The present disclosure relates to the use of a relatively small number of sensors which are able to accurately determine a degree of tilt of a patient support apparatus comprising a patient support surface. The sensor arrangement of the present disclosure provides a simple, cost effective, and accurate measurement of tilt.

By using sensors configured to provide signals indicative of distances between regions of the underside of the patient support apparatus and fixed locations underneath the patient support apparatus, a direct measurement of the height, and thus position, of the patient positioning surface can be obtained. The degree of tilt of the support apparatus, whether it be a pitch or a roll angle, can be determined by making use of simple ratios of the measured distances. Thus, the need to infer the tilt angle and/or height of the patient positioning surface via a complex process involving multiple indirect measurements is removed. Positioning and configuring the sensors in this way removes measurement errors and structural stiffness and thus reduces uncertainty in the result.

By making use of signals provided by three appropriately positioned sensors, the degree of both pitch and roll can determined, in addition to the height of any desired location of the patient positioning apparatus or patient positioning surface.

A patient positioning apparatus for a medical device is disclosed herein. The patient positioning device comprises a tiltable patient support apparatus and a sensor arrangement. The sensor arrangement comprises a processor, and a first and a second sensor communicatively coupled to the processor. The sensors are spaced from one another, the first sensor being configured to provide signals indicative of a first distance between a first region of the underside of the patient support apparatus and a first fixed location underneath the patient support apparatus, and the second sensor being configured to provide signals indicative of a second distance between a second region of the underside of the patient support apparatus and a second fixed location underneath the patient support apparatus. The processor is configured to determine, based on signals from the sensors, a degree of tilt of the patient support apparatus.

Optionally, the first and second fixed locations are located substantially at a base of the patient positioning device.

Optionally, the first sensor is located at the first fixed location and the second sensor is located at the second fixed location.

Optionally, the degree of tilt is determined based on a ratio between the first distance and the second distance.

Optionally, the patient positioning apparatus has a major axis and a minor axis, and the first and second fixed locations are separated along the major axis when the patient positioning apparatus is at zero tilt, such that the processor is configured to determine, based on signals from the sensors, the degree of pitch of the patient support apparatus.

Optionally, the patient positioning apparatus has a major axis and a minor axis, and the first and second fixed locations are separated along the minor axis when the patient positioning apparatus is at zero tilt, such that the processor is configured to determine, based on signals from the sensors, the degree of roll of the patient support apparatus.

Optionally, the apparatus further comprises a third sensor being configured to provide signals indicative of a third distance between a third region of the underside of the patient support apparatus and a third fixed location underneath the patient support apparatus, the first, second and third sensors being positioned to allow the processor to determine, based on signals from the sensors, the degree of both pitch and roll of the patient support apparatus. Optionally, the processor is further configured to determine, based on signals from the first, second and third sensors, the height of a fourth region of the underside of the patient support apparatus; wherein the fourth region lies on a plane defined by the first, second and third regions.

Optionally, the patient positioning apparatus is configured to tilt about a pitch rotation axis and tilt about a roll rotation axis. Optionally, the major axis when the patient positioning apparatus is at zero tilt is parallel with and/or aligns with the roll axis. Optionally, the minor axis when the patient positioning apparatus is at zero tilt is parallel with and/or aligns with the pitch axis. Optionally, the patient support apparatus comprises a patient support base structure and a patient support surface; the patient support surface is tiltable about a roll rotation axis with respect to the base structure; and the apparatus comprises a roll rotation sensor coupled to the processor and configured to provide signals indicative of a distance between a first region of the underside of the patient support surface and a fixed location between the patient support base structure and the patient support surface. Optionally, the processor is configured to determine a degree of pitch of the patient support apparatus based on signals received from the first and second sensors, and a degree of roll based on signals received from the roll rotation sensor.

Optionally, the processor is configured to determine the height of any point of the patient support apparatus along a line joining the first and second regions of the underside of the patient support apparatus based on signals received from the first and second sensors.

Optionally, the apparatus comprises a pitch rotation mechanism configured to tilt the patient support apparatus about a pitch rotation axis.

Optionally, the sensors are configured to measure distances along a direct line of sight.

Optionally, one or more sensors of the sensor arrangement comprise one of an optical sensor, a draw wire sensor, or a linear travel sensor.

Disclosed herein is a method of determining a degree of tilt of a patient support apparatus as disclosed herein, the method comprising: determining the degree of tilt of the patient support apparatus based on signals received from the sensors.

Optionally, the method comprises determining a first value based on signals received from the first sensor, determining a second value based on signals received from the second sensor, and determining the degree of tilt based on a ratio of the first and second value.

Optionally, the patient support apparatus comprises a third sensor configured to provide signals indicative of a third distance between a third region of the underside of the patient support apparatus and a third fixed location underneath the patient support apparatus. The method optionally further comprises: determining, based on signals from the sensors, the degree of both pitch and roll of the patient support apparatus.

Optionally, the method further comprises determining a third value based on signals received from the third sensor; determining the degree of pitch of the patient support apparatus based on the ratio of the first and second value; and determining the degree of roll of the patient support apparatus based on the ratio of the second and third value.

Optionally, the method further comprises determining, based on signals from the first, second and third sensors, the height of a fourth region of the underside of the patient support apparatus; wherein the fourth region lies on a plane defined by the first, second and third regions.

Optionally, the patient support apparatus comprises a patient support base structure and a patient support surface; the patient support surface tiltable about a roll rotation axis with respect to the base structure; and wherein the apparatus comprises a roll rotation sensor coupled to the processor and configured to provide signals indicative of a distance between a first region of the underside of the patient support surface and a fixed location between the patient support base structure and the patient support surface; and the method comprises determining a degree of pitch of the patient support apparatus based on signals received from the first and second sensors, and a degree of roll based on signals received from the roll rotation sensor.

A computer-readable medium is disclosed herein which comprises computer executable instructions which, when performed by a computer, cause the computer to carry out the method.

A Patient Support Apparatus for Tilting a Patient Support Surface with Respect to a Patient Support Base The present application also discloses a patient support apparatus comprising a patient support surface which is tiltable with respect to a patient support base structure. This patient support apparatus may be used in combination with, or separately from, the other arrangements disclosed in this application.

One implementation of such a patient support apparatus 1400 comprises a tiltable patient support surface 1410 that is configured to be tilted with respect to the patient support apparatus 1400. The patient support surface 1410 is configured to be rotated about an axis of rotation referred to herein as a tilt axis. Thus, the patient support surface 1410 may be described as a tiltable patient support surface 1410. In this example, the axis of rotation is parallel to the longitudinal axis of the patient support surface 1410 (roll axis 1120, as shown in FIG. 11). In other examples, the axis of rotation may instead be parallel to the lateral axis of the patient support surface 1410 (pitch axis 1110, as shown in FIG. 11).

In overview, one or more rotary motors are configured to rotate swing elements 1430 positioned underneath the patient support surface 1410, e.g. via rotating drive shafts 1580. The swing elements 1430 each radially extend from a drive shaft 1580 and are coupled to an underside of the patient support surface 1410 at an end distal from the drive shaft. This means that rotation of a swing element 1430 in a first direction will cause the patient support surface 1410 to be pushed upward, and rotating the swing element in a second, opposite direction causes the swing element to be pulled downward. Thus, by controlling the orientation of a plurality of swing elements using the rotary motor(s), the patient support surface 1410 can be moved, and in particular a degree of tilt of the patient support surface can be controlled.

Examples of specific linkages and structures for tilting the patient support surface 1410 will now be described.

Figure 14A:
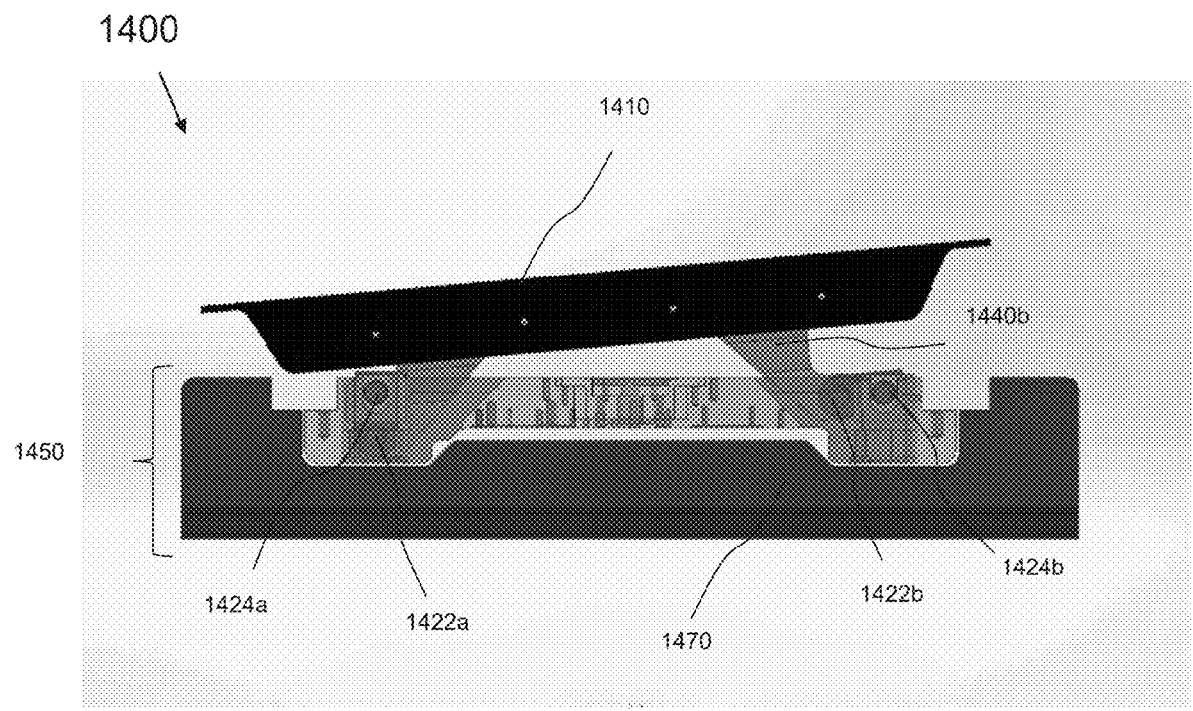
FIGS. 14a and 14b depict a front view of a patient support apparatus 1400 comprising a tiltable patient support surface 1410 in accordance with the present disclosure.
Figure 14B:
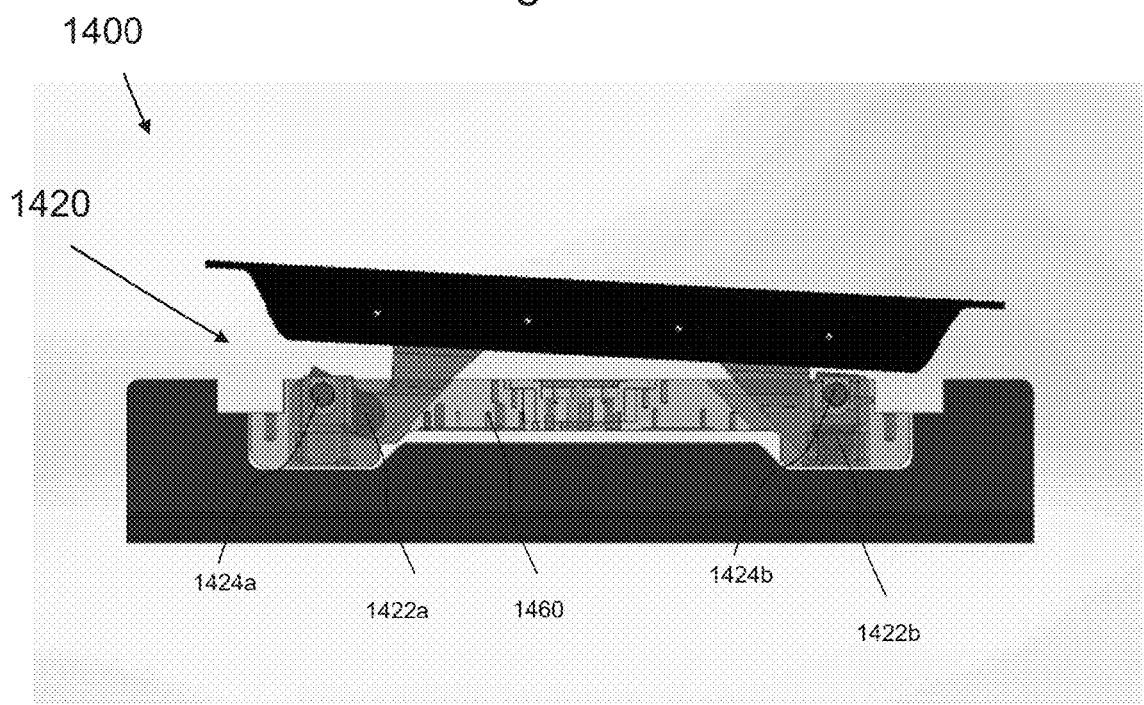

One example of a patient support apparatus 1400 comprising a tiltable patient support surface 1410 is shown in FIG. 14a and FIG. 14b, which show the tiltable patient support surface 1410 in two different tilt positions. These figures show a patient support surface 1410 supported by and connected to a rotation mechanism 1420 comprising first and second swing elements. In this example, the patient support surface 1410 is shown connected to each of the first and second swing elements 1430 by an intermediary (also referred to as a coupling member). As shown, the first swing element 1430 is coupled to a first coupling member 1440 and the second swing element 1430 is connected to a second coupling member 1440. The coupling members 1440 are fixedly connected at a first end to the patient support surface 1410, which is to say that they are connected such that there is little or no movement between the patient support surface 1410 and the coupling members 1440. For example, the coupling members may be screwed or bolted onto the patient support surface 1410. In some examples, the coupling members may therefore be considered to be an extension of the patient support surface 1410 and thus comprised within the patient support surface 1410. In the example shown, the coupling members 1440 are fixably connected or extend from a lower surface of the patient support surface 1410, but they may also be connected to or extend from the sides of the patient support surface 1410.

The coupling members are also rotatably connected (rotationally coupled) at a second end to the first and second swing elements 1430, which is to say that each of the coupling members is configured to rotate relative to a swing element 1430. Each coupling member is configured to rotate about a fixed axis of rotation relative to the swing element to which it is connected, whilst translation between the two parts and rotation about other axes of rotation is otherwise constrained. In the presently described example, the apparatus 1400 comprises first and second swing members 1430 and first and second coupling members 1440, however it is apparent that there may be more than two swing members 1430 and more than two coupling members 1440. The rotational coupling may be achieved using known means, for example, a mechanical bearing such as a pivot connection. In an alternative example, the coupling members 1440 may be rotatably connected to the patient support surface 1410 and have a fixed connection to each of the first and second swing elements. In other examples, there may not be any coupling members and the first and second swing elements 1430 may instead be directly and rotationally coupled to the patient support surface 1410 without the presence of any additional coupling members 1440.

Each of the swing elements 1430 is connected to the patient support base 1450 either directly or indirectly by a connection. The swing elements 1430 are each rotatably coupled to a coupling member at a pivotal axis of rotation

1422. The connection is separated from the pivotal axis of rotation 1422. The axis of rotation about which each of the swing elements 1430 is configured to rotate may be referred to as a swing element axis of rotation 1424. The swing element axis of rotation 1424 is parallel to the tilt axis of the patient support surface 1410. In one example, the rotation mechanism 1420 comprises means for rotating the first and second swing elements 1430 about the swing element axis of rotation 1424. For example, the rotation mechanism 1420 may comprise one or more rotary motors configured to drive the rotation of the first and second swing elements 1430 directly. In another example, the patient support surface 1410 may simply be configured to be tilted by applying an external force to the patient support surface 1410, for example by an operator of the equipment. The axis of rotation 1424 about which the swing element 1430 may be caused to rotate by the rotation mechanism 1420 shall may be referred to herein as the swing element axis of rotation 1424.

As previously described, each swing element 1430 is also rotatably connected to a coupling member 1440 such that the coupling member 1440 is configured to rotate about the swing member. This may also be described as a pivotal connection (the coupling member 1440 is configured to rotate about this pivotal connection) and, as such, the axis of rotation of the pivotal connection may be referred to herein as a pivotal axis of rotation 1422. The swing element axis of rotation 1424 of the first swing element 1430 and the swing element axis of rotation 1424 of the second swing element 1430 are parallel. The pivotal axis of rotation 1422 of the first swing element 1430 and the pivotal axis of rotation 1422 of the second swing element 1430 are parallel. The pivotal axis of rotation 1422 of the first swing element 1430 and the Swing element axis of rotation 1424 of the first swing element 1430 are parallel. The pivotal axis of rotation 1422 of the second swing element 1430 and the swing element axis of rotation 1424 of the second swing element 1430 are parallel.

In summary, the first swing element 1430a is rotatable, by the rotation mechanism 1420, about a first swing element rotation axis 1424a. The first swing element 1430a is rotationally coupled to a first coupling member at a pivotal axis of rotation 1422a. Similarly, the second swing element 1430b is rotatable, by the rotation mechanism 1420, about a second swing element rotation axis 1424b. The second swing element 1430b is rotationally coupled to a second coupling member at a pivotal axis of rotation 1422b.

The first and second swing elements 1430 are connected to the patient support base 1450 at different points on the patient support base. In the implementation depicted in FIGS. 14a,b, the first and second swing elements 1430 are connected to the patient support surface 1410 on opposite sides of the longitudinal centreline of the patient support base to effect a tilt in the form of a roll rotation. Alternatively, the swing elements may be connected on opposite sides of the lateral centreline to effect a tilt in the form of a pitch rotation. In one example, the connection points of the patient support base 1450 to the first and second swing elements 1430 are equidistantly spaced from the longitudinal or lateral centreline of the patient support base.

Each of the swing elements 1430 extends radially outward from its swing element 1430 axis of rotation in a radial direction. The location of the rotational coupling connection between the coupling member 1440 and the swing element 1430 is at the distal end of the swing element 1430 in relation to the swing element 1430 axis of rotation. Thus, for each swing element 1430, the pivotal axis of rotation 1422 and the swing element axis of rotation 1424 are spaced apart from one another. In particular, the pivotal axis of rotation 1422 is located radially outwards with respect to the swing element axis of rotation 1424.

The patient support surface 1410 is connected to the rotation mechanism 1420 and the rotation mechanism 1420 is connected to a patient support base. In one example, the patient support base 1450 comprises a lower base structure 1470 and an upper base structure 1460 that are movably connected to each other, and the rotation mechanism 1420 is connected to the upper base structure 1460. The upper base structure 1460 may be translated linearly with respect to the lower base structure 1470 in the manner described elsewhere herein in relation to other implementations.

Figure 15:
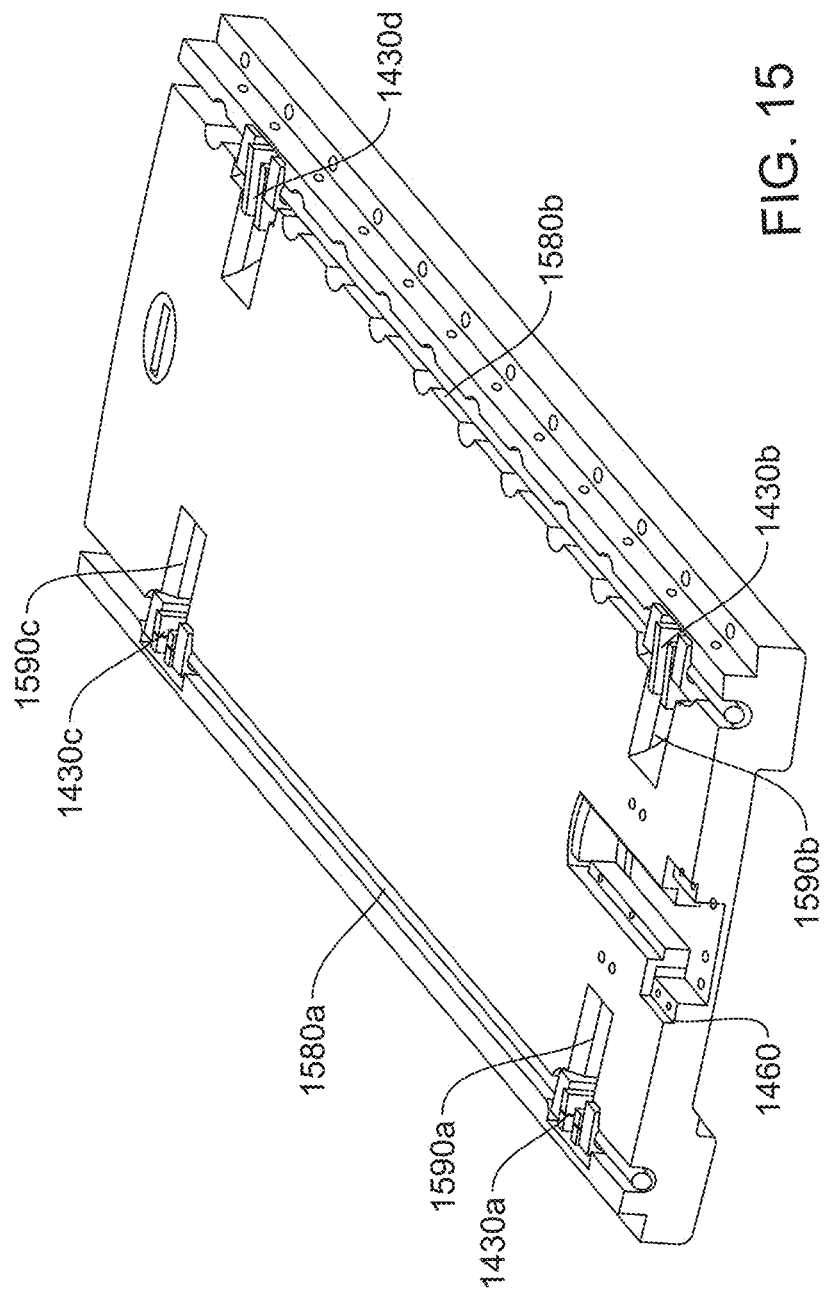
FIG. 15 depicts base structure of a patient support apparatus in accordance with the present disclosure.

In accordance with one example, FIG. 15 depicts a rotation mechanism connected to a patient support base 1450, in particular to an upper base structure 1460. The components will be described generally for the purpose of providing useful accompanying information for the disclosed patient support apparatus 1400. The components of the patient support apparatus 1400 depicted in FIG. 15 are in accordance with the present disclosure and are suitable for use in the disclosed patient support apparatus 1400, although not all of the features/components are necessarily present, or are required to take the specific form depicted in FIG. 15.

The rotation mechanism 1420 illustrated in FIG. 15 comprises four swing elements 1430 connected to the upper base structure. These may be referred to as a first swing element 1430a, a second swing element 1430b, a third swing element 1430c, and a fourth swing element 1430d. The swing elements 1430 are either directly or indirectly connected to the upper base structure 1460 in such a way that the swing elements 1430 are configured to rotate about their swing element axis of rotation 1424 but are otherwise constrained (these may be thought of as connected by a fixed pivot point). Although in this example the swing elements 1430 are in an equidistant and partially symmetric arrangement, one or more of the swing elements 1430 may also not be the same distance from a particular centreline as a swing element 1430 on the other side of the particular centreline. Thus, there is one swing element 1430 in each in each quadrant of the upper base structure 1460 (as shown in FIG. 15).

The rotation mechanism 1420 in this example comprises two drive shafts 1580. A first drive shaft 1580a connects two swing elements 1430a,c on a first lateral side of the upper base structure 1460. A second drive shaft 1580b connects two swing elements 1430b,d on a second, opposite lateral side of the upper base structure 1460. The swing elements 1430 are fixedly connected to the respective drive shafts 1580. The longitudinal axes of both of the swing elements 1430 attached to a particular drive shaft 1580 are parallel to one another.

Figure 16A:
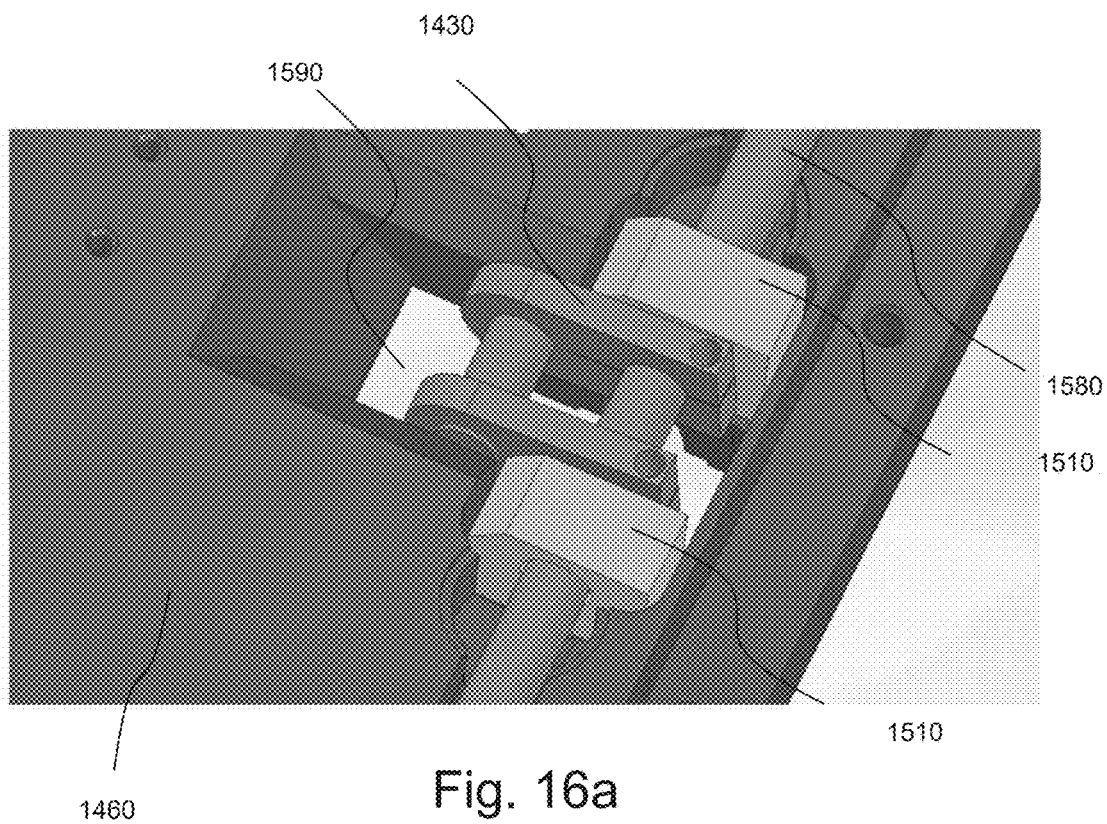
FIGS. 16a and 16b depict a close up view of possible components used to cause tilt of a tiltable patient support surface 1410 in accordance with the present disclosure.
Figure 16B:
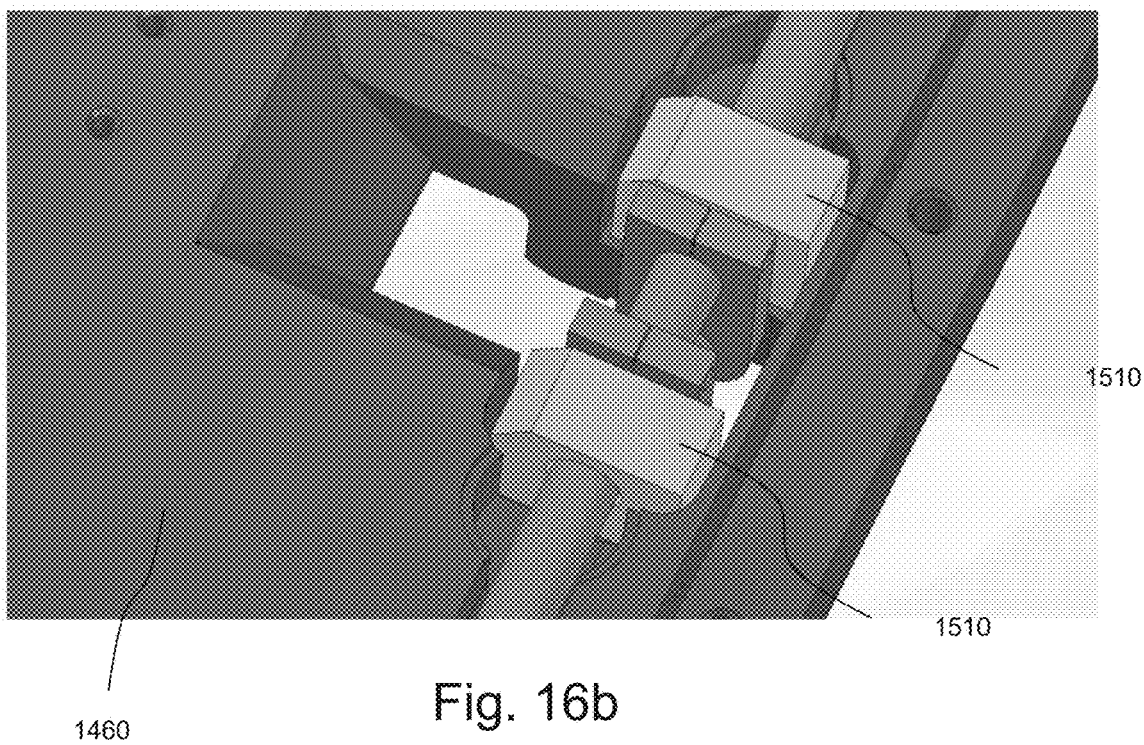

The rotation mechanism 1420 is configured to rotate the drive shafts 1580 to cause the swing elements 1430 to rotate, which in turn causes the patient support surface 1410 to tilt. The two drive shafts 1580 are parallel with one another and, in this example, parallel to the longitudinal axis of the upper base structure. As can be seen in FIG. 15, in a first configuration the two swing elements 1430 connected to the drive shaft 1580 on the left of FIG. 15 both extend downwards (meaning that the pivot point to which a coupling member 1440 may be rotationally coupled is located below the shaft, as also shown in FIG. 16b), whilst the two swing elements 1430 connected to the drive shaft 1580 on the right of FIG. 15 both extend sideways towards the swing elements 1430 connected to the drive shaft 1580 on the left (meaning that the pivot point to which a coupling member 1440 may be rotationally coupled is located to the side of the shaft, as also shown in FIG. 16*a*). The first configuration corresponds to a situation in which the patient support surface 1410 is rolled anticlockwise. In a second configuration, corresponding to a situation where the patient support surface 1410 is rolled clockwise, the situation would be reversed. Having the swing elements 1430 point downwards in a particular configuration allows the total height of the patient support surface 1410 above the patient support base 1450 to be minimised.

The upper base structure 1460 comprises a plurality of slots 1490 that are configured to accommodate the rotation of each of the swing elements 1430 and corresponding coupling members. A first slot 1590*a* is positioned and configured to accommodate the rotation of the first swing element 1430*a*, a second slot 1590*b* is positioned and configured to accommodate the rotation of the second swing element 1430*b*, and so on.

The upper base structure 1460 also comprises first and second longitudinal grooves spaced apart from one another to accommodate the first and second drive shafts 1580. The grooves have a larger diameter than the drive shafts 1580 so as to enable the drive shafts 1580 to freely rotate within the grooves. Setting the drive shafts 1580 into the upper base structure 1460 allows the total height of the patient support surface 1410 above the patient support base 1450 to be minimised.

In one example, the rotation mechanism 1420 comprises one or more rotary motors configured to rotate one or more of the drive shafts 1580. In one example, the patient support apparatus 1400 comprises a controller configured to control the operation of the one or more rotary motors, or other rotational driving means, to cause the rotation of the one or more drive shafts 1580. In one example, the rotary motor may be an appropriately sized electric motor and the controller may be configured to control the rotation of the electric motor. The rotation of, for example the electric motor, or any other rotational driving means may be transferred to the drive shaft 1580 to cause rotation of the drive shaft 1580 by any appropriate means. For example, through the use of one or more cogs, by connection be a chain or belt or by some other means. Thus, the controller may be configured to control the tilt of the patient support surface 1410 by controlling the rotation of the swing elements 1430 to which the patient support surface 1410 may be connected (either directly or indirectly).

A close up of a swing element 1430 in a first and second configuration is depicted in FIG. 16*a* and FIG. 16*b*. In FIG. 16*a*, the swing element 1430 is shown rotated anti-clockwise toward, or at, its maximal rotation position in that direction. In FIG. 16*b*, the swing element 1430 is shown rotated clockwise toward, or at, its maximal rotation position in that direction.

The drive shaft 1580 defines the swing element axis of rotation. The distal end of the swing element 1430 (the end distal to the shaft 1580/swing element rotation axis) is configured to allow rotation of a coupling member 1440 about a pivotal axis of rotation 1422. In one example, shown in FIG. 16*a*, the swing element 1430 is comprised of two parallel parts spatially separated from one another but connected by a bar that lies along a pivotal axis of rotation 1422. This bar may then serve as a pivot point, about which a coupling member 1440 may rotate. It should be understood that the disclosure is not limited to the swing element 1430 comprising two parallel parts. For example, the swing element 1430 may comprise a single part. Many other suitable swing elements 1430 will be apparent to a person skilled in the art.

In one example, the upper base structure 1460 comprises one or more drive shaft holders 1510 configured to support a drive shaft 1580 and restrict movement, apart from rotational motion, of a drive shaft 1580. For example, there may be a drive shaft holder 1510 on either side of a particular swing element 1430, to support the corresponding drive shaft 1580. The drive shaft holder 1510 may be designed to reduce friction on the drive shaft 1580. For example, the drive shaft holder 1510 may comprise a plurality of bearings, or may be lubricated to enable the drive shaft 1580 to easily be rotated.

The swing element 1430 is fixedly connected to the drive shaft 1580, in this example by use of clamping means. The end of the swing element 1430 that is connected to the drive shaft 1580 comprises a hole/aperture for receiving the drive shaft 1580, a slit from that end that extends across the hole and then towards but not as far as the pivot connection point, wherein the swing element 1430 further comprises a bolt hole through both portions of the swing element 1430 (though the swing element 1430 on either side of the slit) at the end with the hole in and on the outside. This allows the swing element 1430 to be threadably fastened so as to clamp onto the drive shaft 1580. In other words, the swing element 1430 is configured as a clamping threaded fastener at one end. In another example, the swing element 1430 may be welded to the drive shaft 1580. Any other appropriate suitable means for achieving a fixed connection may be used and will be apparent to the skilled person.

As described previously with reference to FIG. 15, a swing element 1430 is configured to be rotated from a first configuration to a second configuration, in this example by rotating the drive shaft 1580 to which it is connected. As shown in FIG. 16*a* and FIG. 16*b*, the swing element 1430 may be rotated from a first, horizontal configuration (FIG. 16*a*) to a second vertical configuration (FIG. 16*b*) or vice versa. It will be appreciated that the swing element 1430 may also be rotated by any other amount between these extremes. The rotation of swing elements 1430 that are themselves rotationally coupled, at an end distal to their own axis of rotation, to coupling members fixed on either side of a patient support surface 1410 causes the patient support surface 1410 to tilt in the opposite direction, as can be seen when comparing FIG. 14*a* and FIG. 14*b*. These drawings shown that rotating first and second swing elements 1430 anticlockwise about their respective swing element axis of rotation 1424 (as shown from FIG. 14*a* to FIG. 14*b*), causes the patient support surface 1410, which is rotationally coupled to the first and second swing elements 1430 via first and second coupling members, to rotate in the opposite direction, which in this case is clockwise.

The patient support surface 1410 may also comprise a controller that is configured to control the rotation of the swing elements. For example, by controlling the rotation of one or more drive shafts 1580 to which one or more of the swing elements 1430 are connected. In this way, the controller may control the tilt of the patient support surface 1410. In one example, the tilt of the patient support surface 1410 may be controlled as part of a treatment plan.

The swing elements 1430, coupling members, drive shafts 1580, upper base structure 1460, lower base structure 1470 may be made from any appropriate materials. For example, one or more of these may be made from steel, aluminium, titanium, another metal, plastic, or any other material or indeed from an appropriate combination of materials. The components may be made from materials chosen to enhance stiffness.

The rotation mechanism 1420 illustrated in FIG. 15 comprises four swing elements 1430, but it should be understood that there could also only be two swing elements 1430 or more than four swing elements. In some examples, swing element 1430 may be configured to point up and sideways (rather than down and sideways) which may enable them to attach directly to the patient support surface 1410 without the need for a coupling member 1440 configured to extend underneath the drive shafts 1580.

Disclosed herein is a patient support apparatus comprising a tiltable patient support surface. The apparatus comprises a base structure which comprises a first and a second drive shaft, and one or more rotary motors configured to rotate the first and second drive shafts. The patient support surface comprises a first and a second coupling member, and the coupling members extend from a lower surface of the patient support surface. The first coupling member is rotationally coupled to the first drive shaft via a first swing element and the second coupling member is rotationally coupled to the second drive shaft via a second swing element. Each swing element extends radially outward from its drive shaft and is configured to rotate with the drive shaft. This structure means that, by rotating each of the first and second drive shafts in a first direction, the patient support surface is caused to tilt in the first direction with respect to the base structure, and by rotating each of the first and second drive shafts in a second direction, the patient support surface is caused to tilt in the second direction with respect to the base structure.

Disclosed herein is a patient support apparatus comprising a tiltable patient support surface. The apparatus comprises a base structure which comprises a first and a second drive shaft, and one or more rotary motors configured to rotate the first and second drive shafts. The patient support surface comprises a first and a second coupling member, and the coupling members extend from a lower surface of the patient support surface. The first coupling member is rotationally coupled to the first drive shaft via a first swing element and the second coupling member is rotationally coupled to the second drive shaft via a second swing element. Each swing element extends radially outward from its drive shaft and is configured to rotate with the drive shaft. This structure means that, by rotating each of the first and second drive shafts in a first direction, the patient support surface is caused to tilt in the first direction with respect to the base structure, and by rotating each of the first and second drive shafts in a second direction, the patient support surface is caused to tilt in the second direction with respect to the base structure.

A patient support apparatus for tilting a patient support surface about a tilt axis is disclosed herein, the apparatus comprising: a patient support base; a rotation mechanism comprising a first swing element and a second swing element, wherein each swing element is configured to rotate about its axis of rotation and each swing element extends radially outward from its axis of rotation, wherein the rotation mechanism is configured to rotate the first and second swing elements; and a patient support surface comprising a first and a second coupling member, the first coupling member being rotationally coupled to an end of the first swing element distal to the axis of rotation of the first swing element and the second coupling member being rotationally coupled to an end of the second swing element distal to the axis of rotation of the second swing element, wherein by rotating each swing element in a first direction, the rotation mechanism causes the patient support surface to tilt in a second direction with respect to the base structure, and wherein by rotating each swing element in the second direction, the rotation mechanism causes the patient support surface to tilt in the first direction with respect to the base structure.

Optionally, the rotation mechanism comprises third and fourth swing elements, wherein the rotation mechanism is configured to rotate the third and fourth swing elements, and wherein the patient support surface comprises a third and a fourth coupling member, the third coupling member being rotationally coupled to an end of the third swing element distal to the axis of rotation of the third swing element and the fourth coupling member being rotationally coupled to an end of the fourth swing element distal to the axis of rotation of the fourth swing element.

Optionally, the rotation mechanism comprises first and second drive shafts configured to rotate the first and second swing elements respectively. Optionally, the rotation mechanism comprises first and second drive shafts, wherein the first drive shaft is configured to rotate the first and third swing elements, and wherein the second drive shaft is configured to rotate the second and fourth swing elements. Optionally, the first and second drive shafts are parallel. Optionally, the axis of rotation of the first and second drive shafts is parallel to the tilt axis of the patient support surface. Optionally, the rotation mechanism comprises one or more rotary motors configured to rotate the first and second drive shafts Optionally, each swing element is configured to rotate about its own swing element axis of rotation, wherein each of the swing element axes of rotation is parallel. Optionally, each swing element axis of rotation is perpendicular to the tilt axis of the patient support surface.

Optionally, the tilt axis is one of roll and pitch.

Optionally, each of the coupling members extends from a lower surface of the patient support surface.

Optionally, the patient support base comprises a first and a second longitudinal groove spaced from one another, the first drive shaft positioned at least partly in the first groove and the second drive shaft positioned at least partly in the second groove.

Optionally, the patient support base comprises an upper base structure and a lower base structure, wherein the lower base structure is configured to linearly translate with respect to upper base structure.

Optionally, the first drive shaft and the second drive shafts are located on opposite sides of a longitudinal centreline of the patient support base.

Each of the motors, actuators, and other mechanisms configured to effect movement described herein are controllable by one or more processors. In particular, the height adjustment mechanism and the rotation mechanism are controllable by one or more processors such that these mechanisms can be controlled both independently of one another, and/or together, depending on the requirements of the medical procedure, calibration process, etc.

The approaches described herein, for example positioning control instructions to control the rotation and height adjustment mechanisms, may be embodied on a computer-readable medium, which may be a non-transitory computer-readable medium. The computer-readable medium carrying computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

Figure 17:
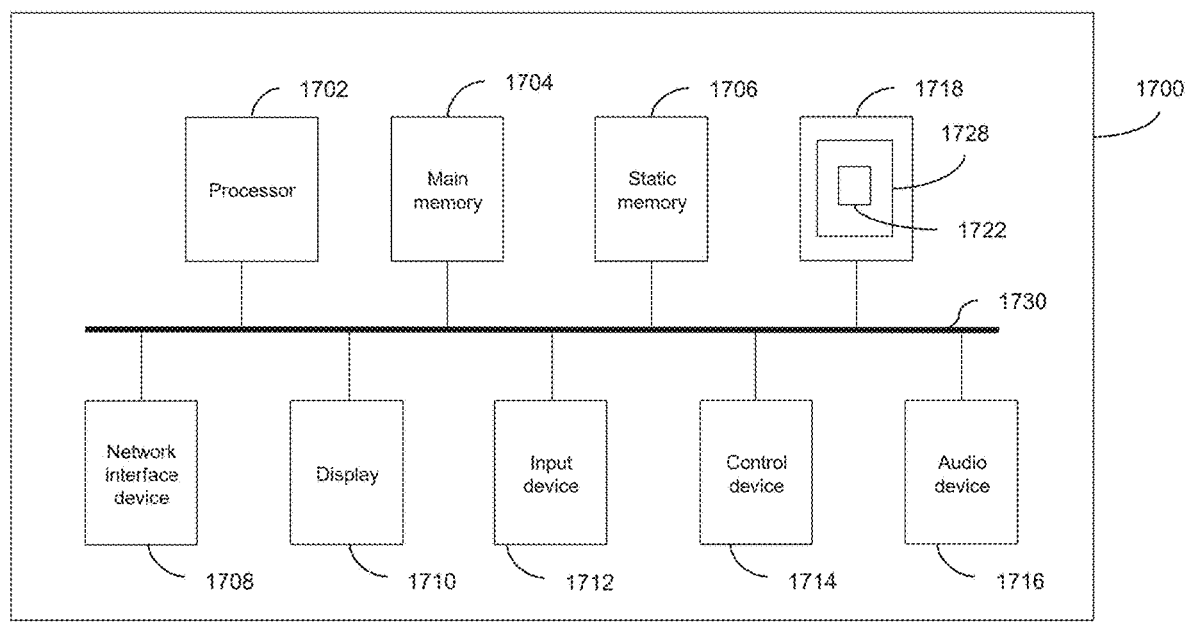
FIG. 17 depicts a block diagram of one implementation of a computing device within which a set of instructions, for causing the computing device to perform any one or more of the methodologies discussed herein, may be executed.

FIG. 17 illustrates a block diagram of one implementation of a computing device 1700 within which a set of instructions, for causing the computing device to perform any one or more of the methodologies discussed herein, may be executed. The computing device 1700 may form part of a radiotherapy device, apparatus, or system. In implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 1700 includes a processing device 1702, a main memory 1704 (e.g., read-only memory (ROM), flash memory, dynamic random access memory (DRAM) such as synchronous DRAM (SDRAM) or Rambus DRAM (RDRAM), etc.), a static memory 1706 (e.g., flash memory, static random access memory (SRAM), etc.), and a secondary memory (e.g., a data storage device 1718), which communicate with each other via a bus 1730.

Processing device 1702 represents one or more general-purpose processors such as a microprocessor, central processing unit, or the like. More particularly, the processing device 1702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1702 may also be one or more special-purpose processing devices such as an application specific integrated circuit (ASIC), a field programmable gate array (FPGA), a digital signal processor (DSP), network processor, or the like. Processing device 1702 is configured to execute the processing logic (instructions 1722) for performing the operations and steps discussed herein.

The computing device 1700 may further include a network interface device 1708. The computing device 1700 also may include a video display unit 1710 (e.g., a liquid crystal display (LCD) or a cathode ray tube (CRT)), an alphanumeric input device 1712 (e.g., a keyboard or touchscreen), a cursor control device 1714 (e.g., a mouse or touchscreen), and an audio device 1716 (e.g., a speaker).

The network interface device 1708 may be located in the treatment room, or in another room such as a nearby room outside the radiotherapy bunker.

The data storage device 1718 may include one or more machine-readable storage media (or more specifically one or more non-transitory computer-readable storage media) 1728 on which is stored one or more sets of instructions 1722 embodying any one or more of the methodologies or functions described herein. The instructions 1722 may also reside, completely or at least partially, within the main memory 1704 and/or within the processing device 1702 during execution thereof by the computer system 1700, the main memory 1704 and the processing device 1702 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining,"

"identifying," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A patient positioning apparatus for a medical device, the patient positioning apparatus comprising:
 a patient support apparatus;
 a support structure configured to extend between the patient support apparatus and a floor of a treatment room to support the patient support apparatus above the floor of the treatment room, wherein the patient support apparatus is rotationally coupled to the support structure; and
 a rotation mechanism comprising a drive member and configured to impart a force, via the drive member, to an underside of the patient support apparatus to thereby rotate the patient support apparatus with respect to the support structure, wherein the rotation mechanism is attached to, and supported by, the support structure, wherein the rotation mechanism comprises an actuation mechanism configured to control movement of the drive member, wherein the drive member comprises an aperture and is rotationally coupled to the support structure via an axle which extends through the aperture, and wherein the actuation mechanism further comprises a motion converter which extends through the aperture and is eccentrically mounted with respect to the axle such that rotation of the motion converter about the axle causes linear movement of the drive member.

2. The apparatus of claim 1, wherein the rotation mechanism is rotationally coupled to the support structure.

3. The apparatus of claim 2, wherein the drive member of the rotation mechanism is rotationally coupled to the support structure.

4. The apparatus of claim 1, wherein the patient support apparatus comprises a patient support surface and a patient support base, the patient support surface being configured to translate linearly with respect to the patient support base, and wherein the support structure is rotationally coupled to the patient support base.

5. The apparatus of claim 1, wherein the support structure comprises a base configured to at least one of make contact with or be embedded in the floor of the treatment room.

6. The apparatus of claim 5, wherein the rotation mechanism is positioned between the patient support apparatus and the base.

7. The apparatus of claim 1, wherein the support structure comprises a height adjustment mechanism configured to control a height of the patient support apparatus above the floor of the treatment room.

8. The apparatus of claim 7, wherein the patient support apparatus is rotationally coupled to the support structure to allow rotation about a principal rotation axis, and wherein controlling the height of the patient support apparatus comprises controlling the height of the principal rotation axis above the floor of the treatment room.

9. The apparatus of claim 8, wherein the height of the patient support apparatus and the rotation of the patient support apparatus are controllable independently of one another.

10. The apparatus of claim 7, the support structure further comprising:
 a support element; and
 a supporting leg, wherein the supporting leg is rotationally coupled to both the patient support apparatus and the support element, and wherein the height adjustment mechanism comprises a motor mechanism configured to rotate the supporting leg with respect to the support element and thereby control the height of the patient support apparatus.

11. The apparatus of claim 10, wherein the rotation mechanism is attached to the support element.

12. The apparatus of claim 1, wherein the actuation mechanism comprises a linear actuator coupled to the motion converter such that actuation of the linear actuator causes the motion converter to rotate about the axle.

13. The apparatus of claim 1, wherein the drive member is coupled to the underside of the patient support apparatus via a coupling element, the drive member being rotationally coupled to the coupling element at a first coupling point and rotationally coupled to the support structure at a second coupling point, and wherein the actuation mechanism is configured to move the drive member by adjusting a distance between the first and the second coupling point.

14. A medical device comprising:
 a patient positioning apparatus, the patient positioning apparatus comprising:
  a patient support apparatus;
  a support structure configured to extend between the patient support apparatus and a floor of a treatment room to support the patient support apparatus above the floor of the treatment room, wherein the patient support apparatus is rotationally coupled to the support structure; and
  a rotation mechanism comprising a drive member and configured to impart a force, via the drive member, to an underside of the patient support apparatus to thereby rotate the patient support apparatus with respect to the support structure, wherein the rotation mechanism is attached to, and supported by, the support structure, wherein the rotation mechanism comprises an actuation mechanism configured to control movement of the drive member, wherein the drive member comprises an aperture and is rotationally coupled to the support structure via an axle which extends through the aperture, and wherein the actuation mechanism further comprises a motion converter which extends through the aperture and is eccentrically mounted with respect to the axle such that rotation of the motion converter about the axle causes linear movement of the drive member.

15. The medical device of claim 14, wherein the medical device is a radiotherapy device.

16. A patient positioning apparatus for a medical device comprising:
- a patient support apparatus, wherein the patient support apparatus comprises a patient support surface and a patient support base, and wherein the patient support surface is configurable to translate linearly with respect to the patient support base;
- a support structure configured to extend between the patient support apparatus and a floor of a treatment room to support the patient support apparatus above the floor of the treatment room, wherein the patient support apparatus is rotationally coupled to the support structure; and
- a rotation mechanism comprising a drive member and configured to impart a force, via the drive member, to an underside of the patient support apparatus to thereby rotate the patient support apparatus with respect to the support structure, wherein the rotation mechanism is attached to, and supported by, the support structure, wherein the rotation mechanism is rotationally coupled to the support structure, wherein the drive member is rotationally coupled to the support structure, wherein the rotation mechanism comprises an actuation mechanism configured to control movement of the drive member, wherein the drive member comprises an aperture and is rotationally coupled to the support structure via an axle which extends through the aperture, and wherein the actuation mechanism further comprises a motion converter which extends through the aperture and is eccentrically mounted with respect to the axle such that rotation of the motion converter about the axle causes linear movement of the drive member.

17. The patient positioning apparatus of claim 16, wherein the support structure is rotationally coupled to the patient support base.

18. The patient positioning apparatus of claim 16, wherein the support structure comprises:
- a height adjustment mechanism configurable to control a height of the patient support apparatus above the floor of the treatment room, wherein the patient support apparatus is rotationally coupled to the support structure to allow for a rotation about a principal rotation axis, and wherein controlling the height of the patient support apparatus comprises controlling the height of the principal rotation axis above the floor of the treatment room.

* * * * *